US012662436B2

(12) United States Patent
Diaz Urrutia et al.

(10) Patent No.: US 12,662,436 B2
(45) Date of Patent: Jun. 23, 2026

(54) PROCESSES FOR DEHYDROGENATING ALKANES AND ALKYL AROMATIC HYDROCARBONS

(71) Applicant: ExxonMobil Chemical Patents Inc., Baytown, TX (US)

(72) Inventors: Christian A. Diaz Urrutia, Auderghem (BE); Xiaoying Bao, Houston, TX (US); Keith H Kuechler, Friendswood, TX (US); Saurabh S. Maduskar, Houston, TX (US); Arun K. Sharma, Hellertown, TX (US); Russell T. Clay, Tomball, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 209 days.

(21) Appl. No.: 18/578,480

(22) PCT Filed: Jul. 20, 2022

(86) PCT No.: PCT/US2022/037683
§ 371 (c)(1),
(2) Date: Jan. 11, 2024

(87) PCT Pub. No.: WO2023/018527
PCT Pub. Date: Feb. 16, 2023

(65) Prior Publication Data
US 2024/0294446 A1      Sep. 5, 2024

Related U.S. Application Data

(60) Provisional application No. 63/328,935, filed on Apr. 8, 2022, provisional application No. 63/231,939, filed on Aug. 11, 2021.

(51) Int. Cl.
*C07C 5/32* (2006.01)

(52) U.S. Cl.
CPC .......... *C07C 5/325* (2013.01); *C07C 2523/42* (2013.01); *C07C 2523/50* (2013.01);
(Continued)

(58) Field of Classification Search
CPC ..... C07C 5/3337; C07C 5/3332; C07C 5/333; C07C 5/325; C07C 11/06; C07C 11/02;
(Continued)

(56) References Cited

U.S. PATENT DOCUMENTS

| | | | |
|---|---|---|---|
| 2,889,383 A | 6/1959 | Green | |
| 6,248,297 B1 | 6/2001 | Stine et al. | |

(Continued)

FOREIGN PATENT DOCUMENTS

| | | | |
|---|---|---|---|
| GB | 1107432 | 3/1968 | |
| KR | 10-0699110 B1 | 3/2007 | |

(Continued)

OTHER PUBLICATIONS

Ray Cocco and Jia Wei Chew, "50 years of Geldart classification," Powder Technology, vol. 428, Article No. 118861, Available online Aug. 2, 2023, <https://doi.org/10.1016/j.powtec.2023.118861!> (12 pages).

*Primary Examiner* — Vishal V Vasisth
(74) *Attorney, Agent, or Firm* — WOMBLE BOND DICKINSON (US) LLP; Kevin Davis

(57)      ABSTRACT

A hydrocarbon can be contacted with dehydrogenation catalyst particles to produce an effluent that can include coked catalyst particles and dehydrogenated hydrocarbon(s). A first stream rich in coked catalyst particles and a second stream rich in dehydrogenated hydrocarbon(s) and containing entrained catalyst particles can be separated from the effluent. The second stream can be contacted with a first quench medium to produce a cooled stream. The cooled stream can be contacted with a second quench medium within a quench
(Continued)

tower. A gaseous stream that includes the dehydrogenated hydrocarbon(s), a first quench medium stream, and a slurry stream that includes the second quench medium and the entrained catalyst particles can be separated from the tower. The first quench medium can be recycled. The entrained catalyst particles can be separated from the slurry to provide recovered second quench medium and recovered entrained catalyst particles. The recovered second quench medium can be recycled.

24 Claims, 4 Drawing Sheets

(52) U.S. Cl.
    CPC ...... *C07C 2523/52* (2013.01); *C07C 2523/62* (2013.01); *C07C 2523/89* (2013.01)
(58) Field of Classification Search
    CPC ............ C07C 2523/14; C07C 2523/52; C07C 2523/62; C07C 2523/50; C07C 2523/42; C07C 2523/58; C07C 2521/10; C07C 2523/89; C07C 2521/04; B01J 37/0201; B01J 23/96; B01J 23/60; B01J 37/0045; B01J 23/007
    See application file for complete search history.

(56) References Cited

U.S. PATENT DOCUMENTS

| | | | |
|---|---|---|---|
| 7,011,740 | B2 | 3/2006 | Tallman et al. |
| 7,473,668 | B2 | 1/2009 | Bartolini et al. |
| 8,653,317 | B2 | 2/2014 | Pierce et al. |
| 10,590,048 | B2 | 3/2020 | Pretz |
| 11,478,769 | B2 | 10/2022 | Pretz |
| 2008/0114197 | A1 | 5/2008 | Bjorklund et al. |
| 2016/0129413 | A1 | 5/2016 | Kulprathipanja et al. |
| 2025/0002429 | A1 | 1/2025 | De Smit |

FOREIGN PATENT DOCUMENTS

| | | |
|---|---|---|
| WO | 2014/081545 | 5/2014 |
| WO | WO2020/191192 | 9/2020 |

PROCESSES FOR DEHYDROGENATING ALKANES AND ALKYL AROMATIC HYDROCARBONS

CROSS-REFERENCE TO RELATED APPLICATIONS

This application is a US national phase application of PCT Application Serial No. PCT/US2022/037683 having a filing date of Jul. 20, 2022, which claims priority to and the benefit of U.S. Provisional Application Nos. 63,231,939 having a filing date of Aug. 11, 2021, and U.S. Provisional Application No. 63,328,935 having a filing date of Apr. 8, 2022, the disclosures of all of which are incorporated herein by reference in their entireties.

FIELD

This disclosure relates to processes for dehydrogenating one or more alkanes and/or alkyl aromatic hydrocarbons. More particularly, this disclosure relates to processes for dehydrogenating one or more alkanes and/or one or more alkyl aromatic hydrocarbons in the presence of fluidized catalyst particles to produce an effluent that includes one or more olefins.

BACKGROUND

The dehydrogenation of alkane and/or alkyl aromatic hydrocarbon feeds provides olefinic slates for the production of a variety of commodity products (construction, packaging, etc.). In particular, the dehydrogenation of propane produces propylene, which is an important intermediate for producing polypropylene. The hydrocarbon feed is introduced into a reactor and contacted with fluidized dehydrogenation catalyst particles at high temperatures allowing for the dehydrogenation of the hydrocarbon feed to produce a conversion effluent. The dehydrogenation process is designed to recover the catalyst particles using one or more cyclones. Catalyst particles that are not collected, however, may need to be recovered for recycling back into the reactor or for metal reclamation, etc.

One way to improve the separation of the catalyst particles from the conversion effluent is to increase the number of cyclones the conversion effluent is passed through. With regard to the composition of the conversion effluent the use of more than two cyclone stages, however, increases the residence time of the conversion effluent at high temperatures and is undesirable because the products and unreacted hydrocarbon feed components can be subjected to further thermal reactions that reduce the yield of the desired products. On the other hand, insufficient separation is also undesirable because any catalyst particles left in the gaseous product stream can cause reverse dehydrogenation when the product stream is quenched and large amounts of catalyst recovered downstream at lower temperatures requires more heat to be input into the process due to the increased amount of catalyst that must be reheated to reaction temperature.

There is a need, therefore, for improved processes for dehydrogenating alkanes and/or alkyl aromatic hydrocarbons to produce a conversion effluent and recovering catalyst particles therefrom. This disclosure satisfies this and other needs.

SUMMARY

Processes for upgrading alkanes and/or alkyl aromatic hydrocarbons are provided. In some embodiments, the process for upgrading a hydrocarbon can include (I) contacting a hydrocarbon-containing feed with fluidized dehydrogenation catalyst particles in a conversion zone to effect dehydrogenation of at least a portion of the hydrocarbon-containing feed to produce a conversion effluent that can include coked catalyst particles and one or more dehydrogenated hydrocarbons. The process can also include (II) separating from the conversion effluent a first stream rich in the coked catalyst particles and lean in the one or more dehydrogenated hydrocarbons and a second stream rich in the one or more dehydrogenated hydrocarbons and containing entrained coked catalyst particles. The process can also include (III) contacting the second stream with a first quench medium to produce a cooled second stream. The process can also include (IV) contacting the cooled second stream with a second quench medium within a quench tower. The process can also include (V) recovering a gaseous stream that can include the one or more dehydrogenated hydrocarbons, a condensed first quench medium stream, and a slurry stream that can include at least a portion of the second quench medium in a liquid phase and the entrained coked catalyst particles from the quench tower. The process can also include (VI) recycling at least a portion of the condensed first quench medium to step (III). The process can also include (VII) separating at least a portion of the entrained coked catalyst particles from the slurry stream to provide a recovered second quench medium stream and a recovered entrained coked catalyst particles stream. The process can also include (VIII) recycling at least a portion of the recovered second quench medium stream to step (IV).

DETAILED DESCRIPTION

Figure 1:
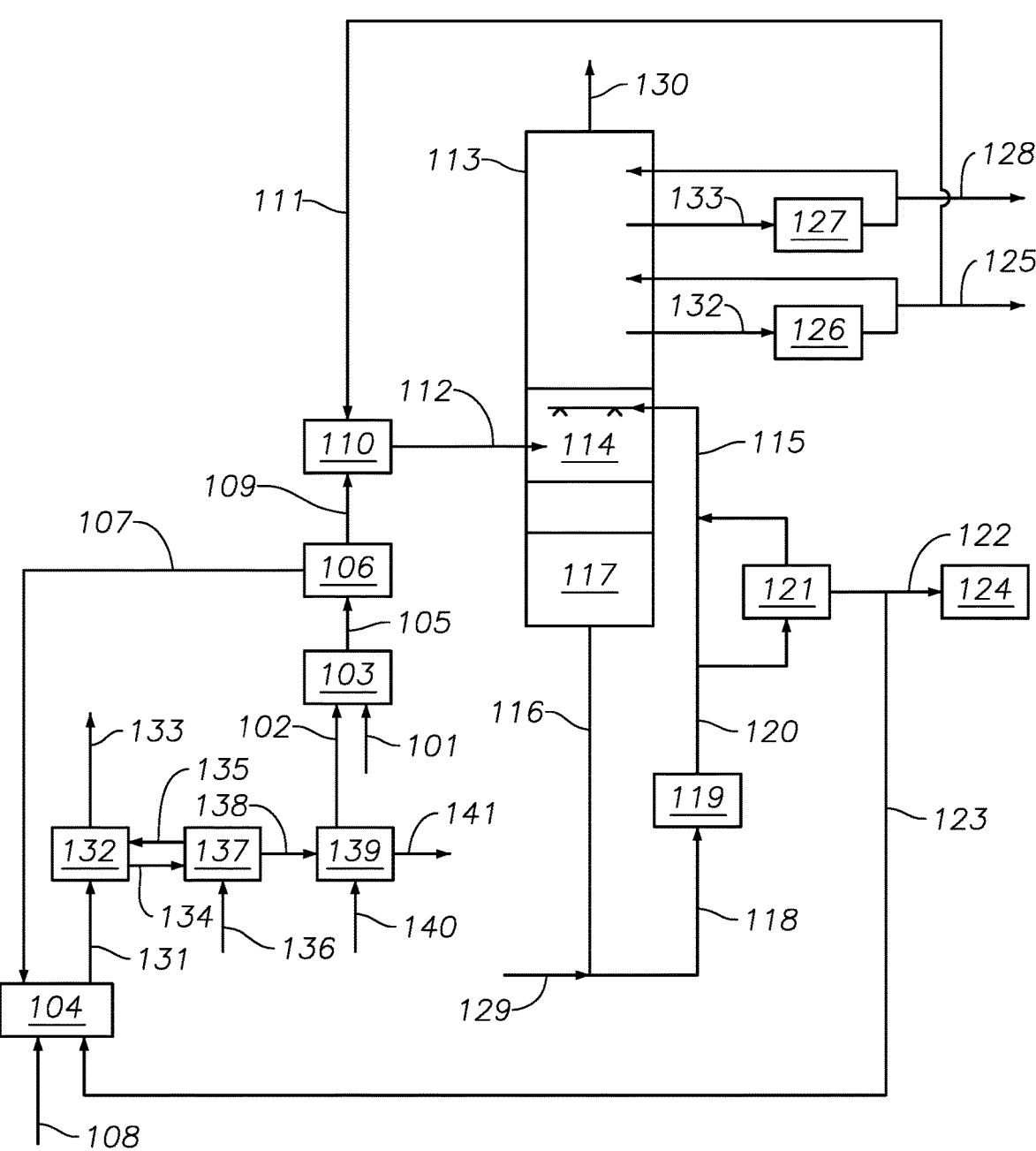
FIG. 1 depicts a system for dehydrogenating a hydrocarbon-containing feed that includes a reactor or conversion zone, a regenerator or combustion zone, and a quench tower, according to one or more embodiments described.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The terms "up" and "down"; "upward" and "downward"; "upper" and "lower"; "upwardly" and "downwardly"; "above" and "below"; and other like terms used herein refer to relative positions to one another and are not intended to denote a particular spatial orientation since the apparatus and methods of using the same may be equally effective at various angles or orientations.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16$^{th}$ Ed., John Wiley & Sons, Inc., (2016), Appendix V. For example, a Group 8 element includes Fe, a Group 9 element includes Co, and a group 10 element includes Ni. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula $$[Mg_{(1-x)}Al_x(OH)_2]\left(A^{n-}_{\frac{x}{n}}\right) \cdot mH_2O],$$

where A is a counter anion of a negative charge n, x is in a range of from >0 to <1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. Yield (carbon mole basis) is conversion times selectivity.

The term "plenum" means a region of a reactor or separator that facilitates fluid communication between pipes or ducts carrying a hot product stream from a reactor or a separator to an outlet. A reactor or separator can have multiple plenums, e.g., a first plenum and a second plenum, and the term plenum will refer to any of the multiple plenums unless otherwise noted.

The term "slurry" means any liquid stream containing fines or solids in an amount of up to 20 wt % based on the weight of the slurry. The term "sludge" means any liquid stream containing fines or solids in a range from >20 wt % to 40 wt % based on the weight of the slurry. The term "cake" means any liquid stream containing fines or solids in an amount of >40 wt % based on the weight of the slurry.

Overview

A hydrocarbon-containing feed can be contacted with fluidized dehydrogenation catalyst particles in any suitable conversion zone to effect dehydrogenation of at least a portion of the hydrocarbon-containing feed to produce a conversion effluent that can include coked catalyst particles and one or more dehydrogenated hydrocarbons. In some embodiments, the one or more dehydrogenated hydrocarbons can be or can include ethylene, propylene, one or more butenes, one or more pentenes, or any mixture thereof. In some embodiments, the conversion effluent can also include benzene. The dehydrogenation catalyst particles can include one or more Group 8-10 elements, e.g., Pt, disposed on a support.

A first stream rich in the coked catalyst particles and lean in the one or more dehydrogenated hydrocarbons and a second stream rich in the one or more dehydrogenated hydrocarbons that includes entrained coked catalyst particles can be separated or otherwise obtained from the conversion effluent. In some embodiments, the first stream and the second stream can be separated from the conversion effluent within one or more separation devices or gas/solid separators. In some embodiments, the first stream and the second stream can be separated from the conversion effluent via one or more cyclones. In some embodiments, the first stream and the second stream can be separated from the conversion effluent in a primary separation device and a secondary separation device downstream of and in fluid communication with the primary separation device, e.g., a primary cyclone and a secondary cyclone. In some embodiments, the first stream and the second stream can be separated from the conversion effluent in a primary separation device. In some embodiments, multiple primary separation devices can be arranged in parallel. In some embodiments, multiple secondary separation devices can be arranged in parallel. In some embodiments, multiple primary separation devices can be arranged in parallel, multiple secondary separation devices can be arranged in parallel, and the multiple secondary separation devices arranged in parallel can be arranged downstream of the multiple primary separation devices arranged in parallel.

The second stream can be contacted with a first quench medium to produce a cooled second stream. For example, when the separation device or gas/solid separator is a cyclone, the second stream can be contacted with the first quench medium within a plenum of the cyclone or a transfer line in fluid communication with the plenum to produce the cooled second stream. The cooled second stream can be contacted with a second quench medium within the quench tower. A gaseous stream substantially free or free of the entrained coked catalyst particles that includes the one or more dehydrogenated hydrocarbons can be recovered as an overhead from the quench tower. A condensed first quench medium stream can be recovered as a side draw from the quench tower and at least a portion of the condensed first quench medium can be recycled to contact an additional quantity of the second stream to produce an additional cooled quantity of the second stream. A slurry stream that can include at least a portion of the second quench medium and the entrained coked catalyst particles can be recovered as a bottoms stream from the quench tower. In some embodiments, a bottom zone within the quench tower can contain an inventory of the slurry stream such that the slurry stream recovered from the quench tower can be drawn from the inventory. In some embodiments, the second stream can be contacted with a first quench medium to produce a cooled second stream right after the second stream exits the primary separation device or right before the second stream enters into the secondary separation device. The cooled second stream can then enter the one or more secondary separation devices before it is contacted with a second quench medium within the quench tower.

At least a portion of the entrained coked catalyst particles can be separated from the slurry to provide a recovered second quench medium lean in or free of any entrained coked catalyst particles and a recovered entrained coked catalyst particles stream. In some embodiments, at least a portion of the recovered second quench medium can be recycled to the quench tower to contact an additional quantity of the cooled second stream therein.

In some embodiments, the catalyst particles disclosed herein may exhibit improved activity and selectivity after undergoing an additional reduction step prior to recontact with the additional quantity of the hydrocarbon-containing feed. Additionally, the post-reduced catalyst particles may maintain the improved activity and selectivity for 10 minutes or more in the presence of the hydrocarbon-containing feed. Accordingly, in some embodiments the process can optionally include contacting at least a portion of the regenerated catalyst particles with a reducing gas to produce regenerated and reduced catalyst particles. In this embodiment, the additional quantity of the hydrocarbon-containing feed can be contacted with at least a portion of the regenerated and reduced catalyst particles to produce the additional conversion effluent. In other embodiments, the process can include contacting at least a portion of the regenerated catalyst particles and at least a portion of the regenerated and reduced catalyst particles with the additional quantity of the hydrocarbon-containing feed to produce the additional conversion effluent. In still other embodiments, the process can include contacting at least a portion of the regenerated catalyst particles, at least a portion of the regenerated and reduced catalyst particles, and/or new or make-up catalyst particles to produce the additional conversion effluent.

Hydrocarbon Dehydrogenation Process

The hydrocarbon-containing feed can be contacted with the dehydrogenation catalyst particles within any suitable conversion zone to effect dehydrogenation of at least a portion of the hydrocarbon-containing feed to produce the conversion effluent that can include the coked catalyst particles and the one or more dehydrogenated hydrocarbons. The hydrocarbon-containing feed can be or can include, but is not limited to, one or more alkanes, e.g., $C_2$-$C_{16}$ linear or branched alkanes and/or $C_4$-$C_{16}$ cyclic alkanes, and/or one or more alkyl aromatic hydrocarbons, e.g., $C_8$-$C_{16}$ alkyl aromatic hydrocarbons. In some embodiments, the hydrocarbon-containing feed and the dehydrogenation catalyst particles can be contacted in a conversion zone disposed within a continuous type process commonly employed in fluidized bed reactors. In some embodiments, the conversion zone can be disposed within a riser reactor. In other embodiments, the conversion zone can be disposed within a downer reactor. In still other embodiments, the conversion zone can be disposed within a vortex reactor. In other embodiments, the conversion zone can be disposed within a reactor and can allow the fluidized dehydrogenation catalyst particles to form a relatively dense turbulent fluidized bed therein during contact with the hydrocarbon-containing feed. A relatively dense turbulent fluidized bed refers to a fluidized bed that is at a superficial gas velocity above the transition velocity designated as the critical velocity between the transition of a bubbling and turbulent bed, but below the transport velocity that demarcates a fast fluidization or pneumatic transport regime in which the dehydrogenation catalyst particles are conveyed such as in a riser reactor. In other embodiments, the conversion zone can be disposed with a dehydrogenation reactor that includes a lower section operating as a fast fluidized or turbulent bed, and an upper section operating as a riser, where the average catalyst flow and the average gas flow are concurrently upward.

Any number of reactors can be operated in series and/or in parallel. Any two or more types of reactors can be used in combination with one another. If two or more reactors are used the reactors can be operated at the same conditions and/or different conditions and can receive the same hydrocarbon-containing feed or different hydrocarbon-containing feeds. If two or more reactors are used the reactors can be arranged in series, in parallel, or a combination thereof with respect to one another. In some embodiments, suitable reactors can be or can include, but are not limited to, high gas velocity riser reactors, high gas velocity downer reactors, vortex reactors, reactors having a relatively dense fluidized catalyst bed at a first or bottom end and relatively less dense fluidized catalyst within a riser located at a second or top end, multiple riser reactors and/or downer reactors operated in parallel and/or series operating at the same or different conditions with respect to one another, or combinations thereof.

In some embodiments, the dehydrogenation catalyst particles can be pneumatically moved through the reaction system, e.g., fed into the conversion zone, fed into the combustion zone, transported through conduits connecting two or more locations, and the like, via a carrier fluid or transport fluid. The transport fluid can be or can include, but is not limited to, a diluent, one or more of the reactants in gaseous form, i.e., the one or more $C_2$-$C_{16}$ alkanes, the one or more $C_8$-$C_{16}$ alkyl aromatic hydrocarbons, the one or more dehydrogenated hydrocarbons, or a mixture thereof. Suitable transport fluids can be or can include, but are not limited to, molecular nitrogen, and volatile hydrocarbons such methane, ethane, and/or propane, argon, carbon monoxide, carbon dioxide, steam, and the like. The amount of transport fluid can be sufficient to maintain the dehydrogenation catalyst particles in a fluidized state and to transport the dehydrogenation catalyst particles from one location, e.g., the combustion zone, to a second location, e.g., the conversion zone. In some embodiments, a weight ratio of the dehydrogenation catalyst particles to the transport fluid can be in a range from 5, 10, 15, or 20 to 50, 60, 80, 90, or 100. Injection points for the transport fluid, as can be made at multiple points along any one or more transfer lines that connect any two zones or other locations such as the combustion zone and the conversion zone.

The hydrocarbon-containing feed and dehydrogenation catalyst particles can be contacted at a temperature in a range from 300° C., 350° C., 400° C., 450° C., 500° C., 550° C., 600° C., 620° C., 630° C., 640° C., 650° C., 660° C., 670° C., 680° C., 690° C., or 700° C. to 725° C., 750° C., 760° C., 780° C., 800° C., 825° C., 850° C., 875° C., or 900° C. In some embodiments, the hydrocarbon-containing feed and dehydrogenation catalyst particles can be contacted at a temperature of at least 620° C., at least 630° C., at least 640° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. In some embodiments, the hydrocarbon-containing feed can be introduced into the conversion zone and contacted with the dehydrogenation catalyst particles therein for a time period of ≤5 hours, ≤4 hours, or ≤3 hours, ≤1 hour, ≤0.5 hours, ≤0.1 hours, ≤3 minutes, ≤1 minute, ≤30 seconds, or ≤0.1 second. In other embodiments, the hydrocarbon-containing feed can be introduced into the conversion zone and contacted with the dehydrogenation catalyst particles therein for a time period in a range from 0.1 seconds, 1 second, 1.5 seconds, 2 seconds, or 3 seconds to 5 seconds, 10 seconds, 20 seconds, 30 seconds, 45 seconds, 1 minute, 1.5 minutes, 2 minutes, 2.5 minutes, or 3 minutes. In some embodiments, the average residence time of the dehydrogenation catalyst particles within the conversion zone can be ≤7 minutes, ≤6 minutes, ≤5 minutes, ≤4 minutes ≤3 minutes, ≤2 minutes, ≤1.5 minutes, ≤1 minute, ≤45 seconds, ≤30 seconds, ≤20 seconds, ≤15 seconds, ≤10 seconds, ≤7 seconds, ≤5 seconds, ≤3 seconds, ≤2 seconds, or ≤1 second. In some embodiments, the average residence time of the dehydrogenation catalyst particles within the conversion zone can be greater than an average residence time of the gaseous components, e.g., the hydrocarbon-containing feed and the conversion effluent obtained therefrom within the conversion zone.

The hydrocarbon-containing feed and the dehydrogenation catalyst particles can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. In some embodiments, the hydrocarbon partial pressure during contact of the hydrocarbon-containing feed and the dehydrogenation catalyst particles can be in a range from 20 kPa-absolute, 50 kPa-absolute, 100 kPa-absolute, 150 kPa, 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. The hydrocarbon-containing feed and dehydrogenation catalyst particles can be contacted under a single $C_2$-$C_{16}$ alkane, e.g., propane, pressure of at least 20 kPa-absolute, at least 50 kPa-absolute, at least 70 kPa-absolute, at least 100 kPa-absolute, at least 150 kPa-absolute, or at least 250 kPa-absolute to 300 kPa-absolute, 400 kPa-absolute, 500 kPa-absolute, or 1,000 kPa-absolute.

The hydrocarbon-containing feed can be contacted with the dehydrogenation catalyst particles within the conversion zone at any weight hourly space velocity (WHSV) effective for carrying out the dehydrogenation process. In some embodiments, the WHSV can be 0.1 hr$^{-1}$, 0.2 hr$^{-1}$, 0.4 hr$^{-1}$, 0.8 hr$^{-1}$, 2 hr$^{-1}$, 4 hr$^{-1}$, or 8 hr$^{-1}$ to 16 hr$^{-1}$, 32 hr$^{-1}$, 64 hr$^{-1}$, or 100 hr$^{-1}$. In some embodiments, a ratio of the dehydrogenation catalyst particles to a combined amount of any $C_2$-$C_{16}$ alkanes and any $C_8$-$C_{16}$ alkyl aromatic hydrocarbons can be in a range from 1, 3, 5, 10, 15, 20, 25, 30, or 40 to 50, 60, 70, 80, 90, 100, 110, 125, or 150 on a weight to weight basis.

In some embodiments, at least a portion of the fluidized dehydrogenation catalyst particles within the conversion zone can be removed, fed into a heat input device where the dehydrogenation catalyst particles can be heated, and the heated catalyst particles can be fed back into the conversion zone. With the reactions occurring within the conversion zone being endothermic, it can be beneficial to remove a portion of the fluidized dehydrogenation catalyst particles therefrom to further increase the temperature after some contact with the hydrocarbon-containing feed. The heat can be indirectly transferred from any suitable heat transfer medium, provided via an electric heater, or any other suitable heater typically used to indirectly heat catalyst particles. In another embodiment, heat can be applied within the conversion zone directly.

The first stream rich in the coked catalyst particles and lean in the one or more dehydrogenated hydrocarbons and the second stream rich in the one or more dehydrogenated hydrocarbons that includes entrained coked catalyst particles can be separated or otherwise obtained from the conversion effluent via any suitable apparatus. In some embodiments, the first stream and the second stream can be obtained from the conversion effluent via one or more solid-gas impingement separators, e.g., one or more cyclone separators. In some embodiments, the cyclone separator can be or can include a two staged or "coupled" configuration including both positive and negative pressure configurations. In some embodiments, suitable cyclone separators can include those disclosed in U.S. Pat. Nos. 4,502,947; 4,985,136; and 5,248,411. In other embodiments, the first stream and the second stream can be obtained from the conversion effluent via a "T" shaped conduit that can cause a majority of the coked catalyst particles to flow in one direction via gravity and the gaseous components to flow in the other direction.

In some embodiments, the first stream rich in the coked catalyst particles and lean in the one or more dehydrogenated hydrocarbons can include >95%, >96%, >97%, >98%, or >99%, >99.9%, >99.99%, >99.999% of the dehydrogenation catalyst particles in the conversion effluent. As such, in some embodiments, the second stream rich in the one or more dehydrogenated hydrocarbons that includes entrained coked catalyst particles can include >0.001%, >0.005%, >0.01%, >0.05%, >0.1%, >0.5%, >1%, or >1.5% to 3%, 4%, or 5% of the dehydrogenation catalyst particles in the conversion effluent.

The second stream can be contacted with a first quench medium to produce a cooled second stream. For example, when the separation device or gas/solid separator is a cyclone, the second stream can be contacted with the first quench medium within a plenum of the cyclone. When a plurality of cyclones is used in series the second stream can be contacted within a plenum in fluid communication with the last cyclone in the plurality of cyclones. In other embodiments, the second stream can be contacted within a transfer line in fluid communication with an exit of the separation device or gas/solid separator and the quench tower. In some embodiments, the first quench medium can be in a gaseous phase, a liquid phase, or a gaseous phase and liquid phase mixture when contacted with the second stream. In some embodiments, the first quench medium can be in liquid phase when contacted with the second stream and can be completely in a gaseous phase after contacting the second stream.

In some embodiments, the second stream can be at a temperature of ≥600° C., ≥620° C., ≥630° C., ≥640° C., ≥650° C., ≥660° C., ≥670° C., ≥680° C., or ≥700° C. when initially contacted with the first quench medium. In some embodiments, the cooled second stream can be at a temperature that is at least 10° C., at least 20° C., at least 30° C., at least 60° C., 80° C., or at least 100° C. less than the temperature of the second stream prior to contact with the first quench medium. In some embodiments, the cooled second stream can be at a temperature in a range from 500° C., 515° C., 530° C., 550° C., or 560° C. to 575° C., 590° C., 600° C., 610° C., or 620° C. In some embodiments, the cooled second stream can be at a temperature of ≥500° C. or ≥550° C. to <620° C.

The cooled second stream can be contacted with a second quench medium within a contact zone disposed within a quench tower. In some embodiments, the second quench medium can be contacted counter-currently with the cooled second stream within the quench tower. For example, the cooled second stream can be introduced into the quench tower below the second quench medium and flow upwardly within the quench tower and the second quench medium can flow downwardly within the quench tower. In some embodiments, the second quench medium can be introduced into the quench tower via one or more nozzles.

A gaseous stream substantially free or free of the entrained coked catalyst particles that includes the one or more dehydrogenated hydrocarbons can be recovered as an overhead from the quench tower. In some embodiments, a velocity of the gaseous stream in an upper end or zone of the quench tower can be low enough that the coked catalyst particles can no longer remain entrained therein thus causing at least a majority of the entrained catalyst particles to fall downward and become entrained in the second quench medium. In some embodiments, the gaseous stream substantially free of the entrained coked catalyst particles can include <0.001 wt %, <0.01 wt %, <0.1 wt %, <1 wt %, or <10 wt % of any entrained coked catalyst particles. In some embodiments, the gaseous stream can be at a temperature in a range from 50° C., 100° C., or 150° C. to 200° C., 250° C., or 300° C.

A condensed first quench medium stream can be recovered as a side draw from the quench tower and at least a portion of the condensed first quench medium can be recycled to contact an additional quantity of the second stream. In some embodiments, the condensed first quench medium stream can be at a temperature in a range from 50° C., 60° C., or 70° C. to 80° C., 100° C., or 120° C.

A slurry stream that can include at least a portion of the second quench medium and the entrained coked catalyst particles can be recovered as a bottoms stream from the quench tower. In some embodiments, a bottom zone within the quench tower can contain an inventory of the slurry stream such that the slurry stream recovered from the quench tower can be drawn from the inventory. The slurry stream can be at a temperature in a range from 150° C., 200° C., or 250° C. to 300° C., 400° C., or 500° C. when recovered from the quench tower.

In some embodiments, the quench tower can include one or more internal structures that can facilitate separation of the cooled second stream into the gaseous stream, the first quench medium stream, and the slurry stream. Illustrative internal structures can include, but are not limited to, trays, grids, packing, or any combination thereof. Illustrative trays can include, but are not limited to, fixed valve trays, jet tab trays, sieve trays, dual flow trays, baffle trays, angle iron trays, draw off trays, shed deck trays, disk trays, donut trays, side by side-splash trays, or any combination thereof. Suitable fixed valve trays, sieve trays, dual flow trays, and grids can include those disclosed in Distillation Design, Henry Z. Kister, McGraw-Hill Inc., 1992, pages 262 to 265 and pages 464-466. Suitable jet tab trays can include those disclosed in WO Publication No. WO2011/014345. In some embodiments, the quench tower disclosed herein can also be known or referred to as a primary fractionator.

In some embodiments, if the process conditions within the quench tower are such that entrained coked catalyst particles can remain in the gaseous stream recovered as the overhead from the quench tower, the gaseous stream can be subjected to further process. In some embodiments, if the gaseous stream recovered as the overhead from the quench tower includes any entrained coked catalyst particles, the gaseous stream can be further separated via one or more electrostatic precipitators, one or more filters, one or more screens, one or more membranes, wet gas scrubber, contact with an absorbent scavenger, one or more additional quench towers, one or more electrocyclones, one or more hydrocyclones, one or more centrifuges, one or plates or cones, or any combination thereof to remove at least a portion of the entrained coked catalyst particles therefrom.

In some embodiments, if the hydrocarbon-containing feed includes water and/or water is produced during the dehydrogenation reaction such that the conversion effluent contains water, a water stream can be recovered from the quench tower as a second side draw from the quench tower. In such embodiment, the water stream can be removed from the process, a portion of the water stream can be recycled to an upper section of the quench tower to further facilitate separation of the entrained coked catalyst fines, first quench medium, and second quench medium from the conversion effluent within the quench tower, or a combination thereof. In some embodiments, the water stream can also be vaporized and recycled to the inlet of the conversion zone as a co-feed for the hydrocarbon.

The first quench medium and the second quench medium can independently be or include, but are not limited to, one or more aromatic hydrocarbons, water, or a mixture thereof. In some embodiments, the aromatic hydrocarbon can be or can include benzene, one or more mono-substituted benzenes, one or more di-substituted benzenes, one or more poly-substituted benzenes, and/or one or more polyaromatic hydrocarbons having a normal boiling point of <580° C. In some embodiments, the polyaromatic hydrocarbon can have a normal boiling point of <580° C., <550° C., <500° C., <400° C., <300° C., <200° C., or <100° C. Suitable aromatic hydrocarbons can be or can include, but are not limited to, benzene, toluene, cumene, ethylbenzene, xylene, methylethylbenzene, trimethylbenzene, methylnaphthalene, A-100 solvent mixture, A-150 solvent mixture, A-200 solvent mixture, A-250 solvent mixture, middle distillate, ultra-low sulfur diesel, heavy gas oil, or any mixture thereof.

In some embodiments, the second quench medium can have a low surface tension, high thermal stability, and low toxicity. In some embodiments, the first quench medium can be or can include, but is not limited to, benzene and the second quench medium can be or can include, but is not limited to, A-100 solvent mixture, A-150 solvent mixture, A-200 solvent mixture, A-250 solvent mixture, middle distillate, ultra-low sulfur diesel, heavy gas oil, or any mixture thereof.

In some embodiments, a composition of the first quench medium and a composition of the second quench medium can be the same or different. In some embodiments, a composition of the first quench medium and the second quench medium can include one or more components that are the same and one or more components that are different such that a portion of the compositions of the first and second quench mediums are the same and a portion of the compositions of the first and second quench mediums are different. In some embodiments, the second quench medium can have a normal boiling point that is greater than a normal boiling point of the first quench medium. In some embodiments, the second quench medium can have a normal boiling point that is lower than a normal boiling point of the first quench medium. In some embodiments, the first quench medium can be or can include benzene and the second quench medium can include one or more polyaromatic hydrocarbons. In some embodiments, the first quench medium may not be used.

In some embodiments, a weight ratio of the first quench medium to the second stream can be in a range from 0.01, 0.05, or 0.08 to 0.1, 0.2, or 0.3. In some embodiments, a weight ratio of the second quench medium to the cooled second stream can be in a range from 0.01, 0.1, or 0.3 to 0.5, 1, 2, or 5. In some embodiments, a weight ratio of the first quench medium to the second quench medium can be in a range from 0.002, 0.02, or 0.2 to 1, 5, or 10.

At least a portion of the entrained coked catalyst particles can be separated from the slurry to provide a recovered second quench medium lean or free of any entrained coked catalyst particles and a recovered entrained coked catalyst particles stream. In some embodiments, at least a portion of the recovered second quench medium can be recycled to the quench tower to contact an additional quantity of the cooled second stream therein.

In some embodiments, the entrained coked catalyst particles can be separated from the slurry via one or more liquid/solid separation devices. Suitable liquid/solid separation devices can be or can include, but are not limited to, one or more filters, one or more membranes, one or more screens or strainers, one or more separator drums, one or more centrifuges, one or more settling tanks, or any combination thereof. In some embodiments, two or more liquid/solid separation devices can be used in parallel such that at least one first liquid/solid separation device can be operated in a filtration mode while at least one second liquid/solid separation device can be operated in a backwashing mode to remove collected coked catalyst particles therefrom. The filtration and backwashing modes can be periodically alternated. In some embodiments, when two or more filters are used to separate the entrained coked catalyst particles from the slurry the backwashing mode can include at least one compressed gas pulse through the at least one filter that is in the backwashing mode in the reverse flow direction to remove the separated coked catalyst particles therefrom. In some embodiments, a combustion gas recovered from a catalyst regeneration step, with or without an optional step to remove any entrained catalyst particles in the combustion gas, can be used as the gas for backwashing the filters. In some embodiments, a liquid stream can be used for backwashing the filters. In some embodiments, a suitable process for recovering the entrained coked catalyst particles from the slurry can include the process disclosed in U.S. Pat. No. 7,375,143.

In some embodiments, at least a portion of the coked catalyst particles in the recovered entrained coked catalyst particles stream can be conveyed to a metal reclamation facility. In such embodiment, at least a portion of the Group 8-10 element(s) can be recovered from the coked catalyst particles in the recovered entrained coked catalyst particles stream. In some embodiments, the at least a portion of the coked catalyst particles conveyed to the metal reclamation facility can be done so in the form of a sludge or a cake. In some embodiments, the liquid in the sludge or cake can include a portion of the second quench medium. In other embodiments, the entrained coked catalyst particles can be substantially separated from the second quench medium and conveyed in the form of fluidized particles. In still other embodiments, the entrained coked catalyst particles can be substantially separated from the second quench medium and mixed with another liquid medium to form another slurry, a sludge or cake that can be conveyed to the metal reclamation facility. The recovered Group 8-10 element(s) can be reused to make new catalyst particles, purified and sold, for example as a commodity, or used for any other desired purpose.

In some embodiments, at least a portion of the Group 8-10 element(s) can be recovered from the coked catalyst particles via any suitable process or combination of processes. Suitable processes for reclaiming at least a portion of the Group 8-10 element(s) can include, but are not limited to, those described in U.S. Pat. No. 7,033,480; U.S. Patent Application Publication No.: 2004/0219082; Great Britain Patent Application Publication No. GB829972A; Chinese Patent No. CN101760627; and/or Chinese Patent Publication No. CN104831071A.

At least a portion of the coked catalyst particles in the first stream and, optionally, at least a portion of the coked catalyst particles in the recovered entrained coked catalyst particles stream can be contacted with one or more oxidants and, optionally, one or more hydrocarbon fuels in a combustion zone to effect combustion of at least a portion of the coke and, if present, the fuel to produce a combustion effluent that can include regenerated catalyst particles lean in coke and a combustion gas.

The oxidant can be or can include, but is not limited to, molecular oxygen, ozone, carbon dioxide, steam, or a mixture thereof. In some embodiments, an amount of oxidant in excess of that needed to combust 100% of the coke on the coked catalyst particles can be used to increase the rate of coke removal from the catalyst particles, so that the time needed for coke removal can be reduced and lead to an increased yield in the upgraded product produced within a given period of time. The optional fuel can be or can include, but is not limited to, molecular hydrogen, methane, ethane, propane, or a mixture thereof. The optional fuel can be mixed with an inert gas such as argon, neon, helium, molecular nitrogen, methane, or a mixture thereof.

The coked catalyst particles and oxidant and, if present, the fuel can be contacted with one another at a temperature in a range from 500° C., 550° C., 600° C., 650° C., 700° C., 750° C., or 800° C. to 900° C., 950° C., 1,000° C., 1,050° C., or 1,100° C. to produce the regenerated catalyst particles. In some embodiments, the coked catalyst particles and oxidant and, if present, the fuel can be contacted with one another at a temperature in a range from 500° C. to 1,100° C., 600° C. to 1,100° C., 600° C. to 1,000° C., 650° C. to 950° C., 700° C. to 900° C., or 750° C. to 850° C. to produce the regenerated catalyst particles. The coked catalyst particles and oxidant and, if present, the fuel can be contacted with one another under an oxidant partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute.

The coked catalyst particles and oxidant and, if present, the fuel can be contacted with one another for a time period in a range from 15 seconds, 30 seconds, 1 minute, 2 minutes, or 5 minutes to 10 minutes, 20 minutes, 30 minutes, 40 minutes, 50 minutes, or 60 minutes. For example, the coked catalyst particles and oxidant and, if present, the fuel can be contacted with one another for a time period in a range from 2 seconds to 50 minutes, 55 minutes, or 60 minutes. In some embodiments, the coked catalyst particles and oxidant and, if present, the fuel can be contacted for a time period sufficient to remove $\geq 50$ wt %, $\geq 75$ wt %, or $\geq 90$ wt % or $\geq 99$% of any coke disposed on the catalyst particles.

In some embodiments, the time period the coked catalyst particles and oxidant and, if present, the fuel contact one another can be greater than the time period the catalyst particles contact the hydrocarbon-containing feed to produce the conversion effluent. For example, the time period the coked catalyst particles and oxidant and, if present, the fuel contact one another can be at least 50%, at least 100%, at least 300%, at least 500%, at least 1,000%, at least 10,000%, at least 30,000%, at least 50,000%, at least 75,000%, at least 100,000%, at least 250,000%, at least 500,000%, at least 750,000%, at least 1,000,000%, at least 1,250,000%, at least 1,500,000%, at least 1,800,000%, at least 2,500,000%, at least 3,500,000%, or 4,140,000% greater than the time period the catalyst particles contact the hydrocarbon-containing feed to produce the conversion effluent.

Without wishing to be bound by theory, it is believed that at least a portion of the Group 8-10 element, e.g., Pt, disposed on the support in the coked catalyst particles can be agglomerated as compared to the Group 8-10 element disposed on the support in the catalyst particles prior to contact with the hydrocarbon-containing feed. It is believed that during combustion of at least a portion of the coke on the coked catalyst particles that at least a portion of the Group 8-10 element can be re-dispersed about the support. Re-dispersing at least a portion of any agglomerated Group 8-10 element can increase the activity and improve the stability of the catalyst particles over many cycles.

In some embodiments, at least a portion of the Group 8-10 element, e.g., Pt, in the regenerated catalyst particles can be at a higher oxidized state as compared to the Group 8-10 element in the catalyst particles contacted with the hydrocarbon-containing feed and as compared to the Group 8-10 element in the coked catalyst particles. As such, as noted above, in some embodiments the process can optionally include contacting at least a portion of the regenerated catalyst particles with a reducing gas to produce regenerated and reduced catalyst particles. Suitable reducing gases (reducing agent) can be or can include, but are not limited to, molecular hydrogen, carbon monoxide, methane, ethane, ethylene, propane, propylene, steam, or a mixture thereof. In some embodiments, the reducing agent can be mixed with an inert gas such as argon, neon, helium, molecular nitrogen, or a mixture thereof. In such embodiments, at least a portion of the Group 8-10 element in the regenerated and reduced catalyst particles can be reduced to a lower oxidation state, e.g., the elemental state, as compared to the Group 8-10 element in the regenerated catalyst particles. In this embodiment, the additional quantity of the hydrocarbon-containing feed can be contacted with at least a portion of the regenerated catalyst particles and/or at least a portion of the regenerated and reduced catalyst particles.

In some embodiments, the regenerated catalyst particles and the reducing gas can be contacted at a temperature in a range from 400° C., 450° C., 500° C., 550° C., 600° C., 620° C., 650° C., or 670° C. to 720° C., 750° C., 800° C., or 900° C. The regenerated catalyst particles and the reducing gas can be contacted for a time period in a range from 1 second, 5 seconds, 10 seconds, 20 seconds, 30 seconds, or 1 minute to 10 minutes, 30 minutes, or 60 minutes. The regenerated catalyst particles and reducing gas can be contacted at a reducing agent partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute.

In some embodiments, if the hydrocarbon containing fuel is introduced into the combustion zone, the catalyst may become further deactivated as compared to combustion of the coke disposed on the catalyst particles in the absence of the hydrocarbon fuel. In such embodiment, the regenerated catalyst particles can be subjected to dry air soaking to more fully regenerate the catalyst particles and improve the activity thereof. For example, the regenerated catalyst particles can be contacted with an oxidative gas that includes <5 mol %, <3 mol %, <1 mol %, <0.5 mol %, or <0.1 mol % of $H_2O$ at an oxidizing temperature in a range from 620° C., 650° C., 675° C., 700° C., or 750° C. to 775° C., 800° C., 850° C., 900° C., 950° C., or 1,000° C. for a duration of at least 30 seconds, at least 1 minute, or at least 5 minutes to produce more fully regenerated catalyst particles. In some embodiments, the regenerated catalyst particles and the oxidative gas that includes <5 mol % of $H_2O$ can be contacted with one another for a duration of ≤2 hours, ≤1 hour, ≤30 minutes, ≤10 minutes, ≤5 minutes, ≤1 min, ≤30 seconds, ≤10 seconds, ≤5 seconds, or ≤1 second to produce the oxidized precursor catalyst. If the regenerated catalyst particles are contacted with the oxidative gas that includes <5 mol % $H_2O$ and also contacted with the reducing gas to produce regenerated and reduced catalyst particles, the contact with the oxidative gas can occur before contact with the reducing gas.

It has been surprisingly and unexpectedly discovered that contacting the regenerated catalyst produced in the presence of the optional hydrocarbon fuel with the oxidative gas that includes no greater than 5 mol % of $H_2O$ can significantly improve the activity and/or selectivity of the regenerated catalyst. Without wishing to be bound by theory, it is believed that $H_2O$ present in the oxidative gas or produced as a combustion product may significantly reduce the effectiveness of the re-dispersion of the Group 8-10 element, e.g., Pt, and hence the effectiveness of the regenerated catalyst.

In some embodiments, a first portion of the coked catalyst particles in the first stream rich in the coked catalyst particles can be fed into the combustion zone for regeneration of the catalyst particles and a second portion of the coked catalyst particles in the first stream can be recycled directly back into the conversion zone. In some embodiments, if the process includes both regeneration and reduction, a first portion of the coked catalyst particles in the first stream rich in the coked catalyst particles can be fed into the combustion zone for regeneration of the catalyst particles and a second portion of the coked catalyst particles can be fed into the reduction zone. In other embodiments, if the process includes both regeneration and reduction, a first portion of the coked catalyst particles in the first particle stream rich in the coked catalyst particles can be fed into the combustion zone for regeneration of the catalyst particles, a second portion of the coked catalyst particles can be recycled directly back into the conversion zone, and a third portion of the coked catalyst particles can be fed into the reduction zone. In any of these embodiments, on a continuous basis or intermittent basis, a portion of the coked catalyst particles, a portion of the regenerated catalyst particles, and/or a portion of the regenerated and reduced catalyst particles can be removed from the process and new or make-up catalyst particles can be introduced into the process. The removal of catalyst particles can be done as the catalyst particles break down in size, become inactivated, and/or begin to convert the hydrocarbon-containing feed at an undesirable rate of conversion. In some embodiments, at least a portion of any removed catalyst particles can be conveyed to the metal reclamation facility for metal recovery therein.

At least a portion of the coked catalyst particles, at least a portion of the regenerated catalyst particles, at least a portion of the regenerated and reduced catalyst particles, new or make-up catalyst particles, or a mixture thereof can be contacted with the additional quantity of the hydrocarbon-containing feed within the conversion zone to produce the additional conversion effluent. In some embodiments, the cycle time from the contacting the hydrocarbon-containing feed with the catalyst particles to the contacting the additional quantity of the hydrocarbon-containing feed with at least a portion of the regenerated catalyst particles, and/or the regenerated and reduced catalyst particles, and optionally with new or make-up catalyst particles can be ≤5 hours, ≤4 hours, ≤3 hours, ≤2 hours, or ≤70 minutes, e.g., from 1 minute to 70 minutes or 5 minutes to 45 minutes.

In some embodiments, one or more additional feeds, e.g., one or more stripping fluids, can be utilized to remove at least a portion of any entrained gaseous components from the catalyst particles. In some embodiments, the coked catalyst particles can be contacted with a stripping fluid prior to contact with the oxidant to remove at least a portion of any entrained upgraded hydrocarbons and/or molecular hydrogen, and/or other gaseous components. Similarly, the regenerated catalyst particles and/or the regenerated and reduced catalyst particles can be contacted with a stripping gas to remove at least a portion of any entrained combustion gas or reducing gas therefrom. In some embodiments, the stripping gas can be inert under the dehydrogenation, combustion, and/or reducing conditions. Suitable stripping fluids can be or can include, but are not limited to, molecular nitrogen, helium, argon, carbon dioxide, steam, methane, or a mixture thereof. The stripping gas can be contacted with the coked catalyst particles, the regenerated catalyst particles, and/or the regenerated and reduced catalyst particles at a volume ratio of about 0.1 $m^3$ to 10 $m^3$ of stripping gas per cubic meter of catalyst particles.

As noted above, the first cycle begins upon contact of the catalyst particles with the hydrocarbon-containing feed, followed by contact with at least the oxidant to produce the regenerated catalyst particles or at least the oxidant and the optional reducing gas to produce the regenerated and reduced catalyst particles, and the first cycle ends upon contact of the regenerated catalyst particles or the regenerated and reduced catalyst particles with the additional quantity of the hydrocarbon-containing feed. If any sweep fluid is utilized, e.g., to strip residual hydrocarbons from the coked catalyst particles, the time period such sweep fluid is utilized would be included in the cycle time.

In one embodiment, a riser configuration can be implemented in which the hydrocarbon-containing feed can be admixed with a dilution gas and contacted with heated and fluidized catalyst particles within the riser. The dilution gas can be or can include, but is not limited to, molecular nitrogen, methane, steam molecular hydrogen, or a mixture thereof. The combined gas can convect or otherwise convey the fluidized catalyst particles through the riser while contacting and reacting as the mixture flows through the riser to produce the conversion effluent that includes the one or more dehydrogenated hydrocarbons and the coked catalyst particles. A residence time of the hydrocarbon-containing feed and the fluidized catalyst particles can be sufficient to achieve a desired conversion of the hydrocarbon-containing feed to the one or more dehydrogenated hydrocarbons. The specific design of the riser, including fabrication and dimensions, can be dependent, at least in part, on the intended chemistry, but typically can require velocities in excess of 4.5 m/s under average gas composition.

Systems suitable for carrying out the dehydrogenation of the hydrocarbon-containing feed can include systems that are well-known in the art such as the fluidized reactors disclosed in U.S. Pat. Nos. 3,888,762; 7,102,050; 7,195,741; 7,122,160; and 8,653,317; U.S. Patent Application Publication Nos. 2004/0082824; 2008/0194891; and WO Publication Nos. WO2001/85872; WO2004/029178; and WO2005/077867.

Dehydrogenation Catalyst Particles

The dehydrogenation catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of the Group 8-10 element, e.g., Pt, disposed on the support, based on the weight of the support. In some embodiments, the catalyst particles can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 wt % of the Group 8-10 element, e.g., Pt, disposed on the support, based on the weight of the support. In some embodiments, the catalyst particles can include >0.001, >0.003 wt %, >0.005 wt %, >0.007, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of Group 8-10 element disposed on the support, based on the weight of the support. In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt.

In some embodiments, the catalyst particles can optionally include two or more Group 8-10 elements, e.g., Pt and Ni and/or Pd. If two or more Group 8-10 elements are disposed on the support the catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of all Group 8-10 elements disposed on the support, based on the weight of the support. In some embodiments, an active component of the catalyst particles that can be capable of effecting one or more of dehydrogenation of a hydrocarbon feed can include the Group 8-10 element(s).

In some embodiments, the catalyst particles can include a promoter in an amount of up to 10 wt % disposed on the support, based on the weight of the support. The promoter can be or can include, but is not limited to, Sn, Ga, Zn, Ge, In, Re, Ag, Au, Cu, a combination thereof, or a mixture thereof. In at least one embodiment, the promoter can be or can include Sn. In some embodiments, the promoter can be associated with the Pt and/or, if present, the Ni and/or Pd. For example, the promoter and the Pt disposed on the support can form Pt-promoter clusters that can be dispersed on the support. The promoter can improve the selectivity/activity/longevity of the catalyst particles for a given upgraded hydrocarbon. In some embodiments, the promoter can improve the propylene selectivity of the catalyst particles when the hydrocarbon-containing feed includes propane. The catalyst particles can include the promoter in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the catalyst particles can optionally include one or more alkali metal elements in an amount of up to 5 wt % disposed on the support, based on the weight of the support. The alkali metal element, if present, can be or can include, but is not limited to, Li, Na, K, Rb, Cs, a combination thereof, or a mixture thereof. In at least one embodiment, the alkali metal element can be or can include K and/or Cs. In at least some embodiments, the alkali metal element ca be or can include K and/or Cs. In some embodiments, the alkali metal element, if present, can improve the selectivity of the catalyst particles for a given upgraded hydrocarbon. The catalyst particles can include the alkali metal element in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

The support can be or can include, but is not limited to, one or more Group 2 elements, a combination thereof, or a mixture thereof. In some embodiments, the Group 2 element can be present in its elemental form. In other embodiments, the Group 2 element can be present in the form of a compound. For example, the Group 2 element can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element can be present in different forms. For example, a first compound can be an oxide and a second compound can be an aluminate where the first compound and the second compound include the same or different Group 2 element, with respect to one another.

The support can include ≥0.5 wt %, ≥1 wt %, ≥2 wt %, ≥3 wt %, ≥4 wt %, ≥5 wt %, ≥6 wt %, ≥7 wt %, ≥8 wt %, ≥9 wt %, ≥10 wt %, ≥11 wt %, ≥12 wt %, ≥13 wt %, ≥14 wt %, ≥15 wt %, ≥16 wt %, ≥17 wt %, ≥18 wt %, ≥19 wt %, ≥20 wt %, ≥21 wt %, ≥22 wt %, ≥23 wt %, ≥24 wt %, ≥25 wt %, 26 wt %, ≥27 wt %, ≥28 wt %, 29 wt %, 30 wt %, ≥35 wt %, ≥40 wt %, ≥45 wt %, ≥50 wt %, ≥55 wt %, ≥60 wt %, ≥65 wt %, ≥70 wt %, ≥75 wt %, ≥80 wt %, ≥85, or ≥90 wt % of the Group 2 element, based on the weight of the support. In some embodiments, the support can include the Group 2 element in a range from 0.5 wt %, 1 wt %, 2 wt %, 2.5 wt %, 3 wt %, 5 wt %, 7 wt %, 10 wt %, 11 wt %, 13 wt %, 15 wt %, 17 wt %, 19 wt %, 21 wt %, 23 wt %, or 25 wt % to 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or 92.34 wt %, based on the weight of the support. In some embodiments, a molar ratio of the Group 2 element to the Group 8-10 element(s) present can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700, 000, 800,000, or 900,000.

In some embodiments, the support can include the Group 2 element and Al and can be in the form of a mixed Group 2 element/Al metal oxide that has O, Mg, and Al atoms mixed on an atomic scale. In some embodiments, the support can be or can include the Group 2 element and Al in the form of an oxide or one or more oxides of the Group 2 element and $Al_2O_3$ that can be mixed on a nm scale. In some embodiments, the support can be or can include an oxide of the Group 2 element, e.g., MgO, and $Al_2O_3$ mixed on a nm scale.

In some embodiments, the support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support can be or can include, but is not limited to, one or more of the following compounds: $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$, $BaCO_3$; $CaZrO_3$; $Ca_7ZrAl_6O_{18}$; $CaTiO_3$; $Ca_7Al_6O_{18}$; $Ca_7HfAl_6O_{18}$; $BaCeO_3$; one or more magnesium chromates, one or more magnesium tungstates, one or more magnesium molybdates, combinations thereof, and mixtures thereof. In some embodiments, the Group 2 element can include Mg and at least a portion of the Group 2 element can be in the form of MgO or a mixed oxide that includes MgO. In some embodiments, the support can be or can include, but is not limited to, a $MgO$—$Al_2O_3$ mixed metal oxide. In some embodiments, when the support is a $MgO$—$Al_2O_3$ mixed metal oxide, the support can have a molar ratio of Mg to Al equal to 20, 10, 5, 2, 1 to 0.5, 0.1, or 0.01.

The $Mg_wAl_2O_{3+w}$, where w is a positive number, if present as the support or as a component of the support can have a molar ratio of Mg to Al in a range from 0.5, 1, 2, 3, 4, or 5 to 6, 7, 8, 9, or 10. In some embodiments, the $Mg_wAl_2O_{3+w}$ can include MgAl2O4, Mg2Al2O5, or a mixture thereof. The $Ca_xAl_2O_{3+x}$, where x is a positive number, if present as the support or as a component of the support can have a molar ratio of Ca to Al in a range from 1:12, 1:4, 1:2, 2:3, 5:6, 1:1, 12:14, or 1.5:1. In some embodiments, the $Ca_xAl_2O_{3+x}$ can include tricalcium aluminate, dodecacalcium hepta-aluminate, monocalcium aluminate, monocalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support can have a molar ratio of Ba to Al 0.05, 0.3, or 0.6 to 0.9, 1.5, or 3.

In some embodiments, the support can also include, but is not limited to, at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga. If the support also includes a compound that includes the metal element and/or metalloid element selected from Groups other than Group 2 and Group 10, where the at least one metal element and/or at least one metalloid element is not Li, Na, K, Rb, Cs, Sn, Cu, Au, Ag, or Ga, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga can be or can include, but is not limited to, one or more rare earth elements, i.e., elements having an atomic number of 21, 39, or 57 to 71.

If the support includes the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element can, in some embodiments, function as a binder and can be referred to as a "binder". Regardless of whether or not the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element selected from Groups other than Group 2 and Group 10 will be further described herein as a "binder" for clarity and ease of description. It is known that in literature, some of the compounds herein referred to as "binders" may also be referred to as fillers, matrix, an additive, etc. In some embodiments, the support can include the binder in a range from 0.01 wt %, 0.05 wt %, 0.1 wt %, 0.5 wt %, 1 wt %, 5 wt %, 10 wt %, 15 wt %, 20 wt %, 25 wt %, 30 wt %, 35 wt % or 40 wt % to 50 wt %, 60 wt %, 70 wt %, 80 wt %, or 90 wt % based on the weight of the support.

In some embodiments, suitable compounds that include the binder can be or can include, but are not limited to, one or more of the following: $B_2O_3$, $AlBO_3$, $Al_2O_3$, $SiO_2$, $ZrO_2$, $TiO_2$, SiC, $Si_3N_4$, an aluminosilicate, zinc aluminate, ZnO, VO, $V_2O_3$, $VO_2$, $V_2O_5$, $Ga_sO_t$, $In_uO_v$, $Mn_2O_3$, $Mn_3O_4$, MnO, one or more molybdenum oxides, one or more tungsten oxides, one or more zeolites, where s, t, u, and v are positive numbers and mixtures and combinations thereof.

The catalyst particles can have a median particle size in a range from 1 μm, 5 μm, 10 μm, 20 μm, 40 μm, or 60 μm to 80 μm, 100 μm, 115 μm, 130 μm, 150 μm, 200 μm, 300 μm or 400, or 500 μm. The catalyst particles can have an apparent loose bulk density in a range from 0.3 $g/cm^3$, 0.4 $g/cm^3$, 0.5 $g/cm^3$, 0.6 $g/cm^3$, 0.7 $g/cm^3$, 0.8 $g/cm^3$, 0.9 $g/cm^3$, or 1 $g/cm^3$ to 1.1 $g/cm^3$, 1.2 $g/cm^3$, 1.3 $g/cm^3$, 1.4 $g/cm^3$, 1.5 $g/cm^3$, 1.6 $g/cm^3$, 1.7 $g/cm^3$, 1.8 $g/cm^3$, 1.9 $g/cm^3$, or 2 $g/cm^3$, as measured according to ASTM D7481-18 modified with a 10, 25, or 50 mL graduated cylinder instead of a 100 or 250 mL graduated cylinder. In some embodiments, the catalyst particles can have an attrition loss after one hour of ≤5 wt %, ≤4 wt %, ≤3 wt %, ≤2 wt %, ≤1 wt %, ≤0.7 wt %, ≤0.5 wt %, ≤0.4 wt %, ≤0.3 wt %, ≤0.2 wt %, ≤0.1 wt %, ≤0.07 wt %, or ≤0.05 wt %, as measured according to ASTM D5757-11(2017). The morphology of the particles is largely spherical so that they are suitable to run in a fluid bed reactor. In some embodiments, the catalyst particles can have a size and density that is consistent with a Geldart A or Geldart B definition of a fluidizable solid.

In some embodiments, the catalyst particles can have a surface area in a range from 0.1 $m^2/g$, 1 $m^2/g$, 10 $m^2/g$, or 100 $m^2/g$ to 500 $m^2/g$, 800 $m^2/g$, 1,000 $m^2/g$, or 1,500 $m^2/g$. The surface area of the catalyst particles can be measured according to the Brunauer-Emmett-Teller (BET) method using adsorption-desorption of nitrogen (temperature of liquid nitrogen, 77 K) with a Micromeritics 3flex instrument after degassing of the powders for 4 hrs at 350° C. More information regarding the method can be found, for example, in "Characterization of Porous Solids and Powders: Surface Area, Pore Size and Density," S. Lowell et al., Springer, 2004.

The preparation of the support can be accomplished via any known process. For simplicity and ease of description, the preparation of a suitable support that includes a mixed oxide of magnesium and aluminum (Mg(Al)O or MgO/$Al_2O_3$) support will be described in more detail. Catalyst synthesis techniques are well-known and the following description is for illustrative purposes and not to be considered as limiting the synthesis of the support or the catalyst particles. In some embodiments, to make the MgO/$Al_2O_3$ mixed oxide support, Mg and Al precursors such as $Mg(NO_3)_2$ and $Al(NO_3)_3$ can be mixed together, e.g., ball-milled, followed by calcination to produce the support. In another embodiment, the two precursors can be dissolved in $H_2O$, stirred until dry (with heat optionally applied), followed by calcination to produce the support. In another embodiment, the two precursors can be dissolved in $H_2O$, followed by the addition of a base and a carbonate, e.g., $NaOH$/$Na_2CO_3$ to produce hydrotalcite, followed by calcination to produce the support. In another embodiment, a commercial ready MgO and $Al_2O_3$ may be mixed and ball-milled to produce the support. In another embodiment, the $Mg(NO_3)_2$ precursor can be dissolved in $H_2O$ and the solution can be impregnated onto an existing support, e.g., an $Al_2O_3$ support, that can be dried and calcined to produce the support. In another embodiment, Mg from $Mg(NO_3)_2$ can be loaded onto an existing $Al_2O_3$ support through ion adsorption, followed by liquid-solid separation, drying and calcination to produce the support. Without wishing to be bound by theory, it is believed that the support produced via any one of the above methods and/or other methods can include (i) the Mg and Al mixed together on the nm scale, (ii) the Mg and Al in the form of a mixed Mg/Al metal oxide, or (iii) a combination of (i) and (ii).

Group 8-10 metals and any promoter and/or any alkali metal element may be loaded onto the mixed oxide support by any known technique. For example, one or more Group 8-10 element precursors, e.g., chloroplatinic acid, tetramineplatinum nitrate, and/or tetramineplatinum hydroxide, one or more promoter precursors (if used), e.g., a salt such as $SnCl_4$ and/or $AgNO_3$, and one or more alkali metal element precursors (if used), e.g., $KNO_3$, KCl, and/or NaCl, can be dissolved in water. The solution can be impregnated onto the support, followed by drying and calcination. In some embodiments, the Group 8-10 element precursor and optionally the promoter precursor and/or the alkali metal element precursor can be loaded onto the support at the same time, or separately in a sequence separated by drying and/or calcination steps. In other embodiments, the Group 8-10 element and, optionally the promoter and/or alkali metal element, can be loaded onto the support by chemical vapor deposition, where the precursors are volatilized and deposited onto the support, followed by calcination. In other embodiments, the Group 8-10 element precursor and, optionally, the promoter precursor and/or alkali metal precursor, can be loaded onto the support through ion adsorption, followed by liquid-solid separation, drying and calcination. Optionally, the catalyst particles can also be synthesized using a one-pot synthesis method where the precursors of the support, group 8-10 metal active phase and the promoters are all mixed together, dry or wet, with or without any other additives to aid the synthesis, followed by drying and calcination.

In some embodiments, the catalyst particles can be formulated into Geldart A or B type particles via the well-known spray drying process. Spray-dried catalyst particles having an average cross-sectional area in a range from 20 μm, 40 μm, or 50 μm to 80 μm, 90 μm, or 100 μm are typically used in an FCC type fluid-bed reactor. To make spray-dried catalyst particles, the support, the Group 8-10 element, and any additional components, e.g., the promoter and/or the alkali metal, can be made into a slurry with binder/additive in the slurry before spray-drying and calcination. Alternatively, the Group 8-10 element, and any additional components, e.g., the promoter and/or the alkali metal, can be added to the formulated support to produce the formulated catalyst particles.

Suitable processes that can be used to prepare the catalyst particles disclosed herein can include the processes described in U.S. Pat. Nos. 4,788,371; 4,962,265; 5,922, 925; 8,653,317; EP Patent No. EP0098622; Journal of Catalysis 94 (1985), pp. 547-557; and/or Applied Catalysis 54 (1989), pp. 79-90.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst particles. In some embodiments, the hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatic hydrocarbons can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the hydrocarbon-containing feed can be diluted with one or more diluents gases. Suitable diluents can be or can include, but are not limited to, argon, neon, helium, molecular nitrogen, carbon dioxide, methane, molecular hydrogen, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatic hydrocarbons in the hydrocarbon-containing feed. When the diluent includes molecular hydrogen, a molar ratio of the molecular hydrogen to a combined amount of any $C_2$-$C_{16}$ alkane and any $C_8$-$C_{16}$ alkyl aromatic hydrocarbons can be in a range from 0.1, 0.3, 0.5, 0.7, or 1 to 2, 3, 4, 5, 6, 7, 8, 9, or 10. In some embodiments, if the diluent is used, the diluent can be mixed with the hydrocarbon-containing feed and/or introduced or otherwise fed into the conversion zone as a separate feed via one or more inlets dedicated to feeding the diluent into the conversion zone. Similarly, the hydrocarbon-containing feed can also be introduced into the conversion zone via one or more inlets dedicated to feeding the hydrocarbon-containing feed into the conversion zone.

In some embodiments, the hydrocarbon-containing feed can be substantially free of any water or steam, e.g., <0.1 vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include ≤50 vol %, ≤45 vol %, ≤40 vol %, ≤35 vol %, ≤30 vol %, ≤25 vol %, ≤20 vol %, or ≤15 vol % of water or steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of water or steam, based on a total volume of any $C_2$-$C_{16}$ alkanes and any $C_8$-$C_{16}$ alkyl aromatic hydrocarbons in the hydrocarbon-containing feed. Similar to the diluent, if water or steam is fed into the conversion zone, the water or steam can be fed into the conversion zone as a component of the hydrocarbon-containing feed or via one or more separate inlets dedicated to introducing the steam into the conversion zone.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof. In some embodiments, the sulfur can be introduced into the conversion zone as a separate feed, as a component of the diluent if used, and/or as a component of the steam if used.

The hydrocarbon-containing feed can be substantially free or free of molecular oxygen. In some embodiments, the hydrocarbon-containing feed can include ≤5 mol %, ≤3 mol %, or ≤1 mol % of molecular oxygen ($O_2$). It is believed that providing a hydrocarbon-containing feed substantially-free of molecular oxygen substantially prevents oxidative coupling reactions that would otherwise consume at least a portion of the alkane and/or the alkyl aromatic hydrocarbon in the hydrocarbon-containing feed.

Recovery and Use of the Dehydrogenated Hydrocarbons

The conversion effluent can include at least one olefin, water, unreacted hydrocarbons, unreacted molecular hydrogen, etc. The olefin(s) can be recovered or otherwise obtained via any convenient process, e.g., by one or more conventional processes. One such process can include cooling the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters can be used to separate the dehydrogenated product from the unreacted hydrocarbon-containing feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

Exemplary Embodiments

FIG. 1 depicts a system for dehydrogenating a hydrocarbon-containing feed in line 101 that includes a reactor or conversion zone 103, a regenerator or combustion zone 104, an oxygen soaking zone 137, a reduction zone 139 and a quench tower 113, according to one or more embodiments. The hydrocarbon-containing feed via line 101 can be introduced into the conversion zone 103, e.g., at a bottom end of a riser reactor or an upper end of a downer reactor. In some embodiments, the hydrocarbon-containing feed in line 101 can include steam. Regenerated and reduced catalyst particles via line 102 can be conveyed from the reduction zone 139 to the conversion zone 103. The hydrocarbon-containing feed can be contacted with the regenerated and reduced catalyst particles in the conversion zone 103 to effect dehydrogenation of at least a portion of the hydrocarbon-containing feed to produce a conversion effluent via line 105 that can include coked catalyst particles, one or more dehydrogenated hydrocarbons, unreacted hydrocarbon-containing feed, steam, benzene, or any mixture thereof.

The conversion effluent via line 105 can be introduced into one or more separation devices 106, e.g., one or more cyclones, that can separate the conversion effluent into a first stream 107 rich in the coked catalyst particles and lean in the one or more dehydrogenated hydrocarbons and a second stream via line 109 rich in the one or more dehydrogenated hydrocarbons that includes entrained coked catalyst particles.

The first stream via line 107 can be recycled to the combustion zone 104. In some embodiments, the first stream in line 107 can include entrained gaseous components such as the one or more dehydrogenated hydrocarbons, unreacted hydrocarbon-containing feed, steam, or a mixture thereof. In such embodiment, at least a portion of the gaseous components in the first stream in line 107 can be stripped off before the first stream is introduced into the combustion zone 104. An oxidant and optionally a fuel via line 108 can be introduced into the combustion zone 104 that can contact at least a portion of the coked catalyst particles in the first stream to effect combustion of at least a portion of the coke, and, if present, the fuel to produce a combustion effluent that includes the regenerated catalyst particles and a combustion gas. The combustion of the coke and, if present fuel, can produce heat to burn the coke from the coked catalyst particles, re-disperse the Group 8-10 element(s) on the spent catalyst particles and add heat to the regenerated catalyst particles.

The combustion effluent can be recovered via line 131 and can enter into one or more separation devices 132, e.g., one or more cyclones, to be separated into stream 134 that contains a majority of any catalyst particles in the combustion effluent and a small amount of entrained combustion gas and combustion gas stream 133 that contains a majority of the combustion gas and, if any, a small amount of entrained catalyst particles. In some embodiments, the one or more separation devices 132 can include three or more stages of cyclones to achieve a higher solid recovery efficiency from the combustion effluent in line 131 and to reduce the amount of entrained catalyst particles in the combustion gas stream 133. Stream 134 can be sent to an oxygen soaking zone 137. A relatively dry oxidant gas stream 136 can be fed into the oxygen soaking zone 137 to fully regenerate the catalyst. After entering into zone 137, any un-reacted dry oxidant gas stream can entrain fully regenerated catalyst particles and exit zone 137 as stream 135. Stream 135 can enter into the separation device 132 and be split into a solid stream and a gas stream. The solid stream rich in fully regenerated catalyst particles can join stream 134 and return to zone 137. The gas stream rich in the unreacted dry oxidant gas can join stream 133. The fully regenerated catalyst particles can leave zone 137 as stream 138 and enter into the reduction zone 139. A reduction gas stream 140 can also be fed into zone 139. The regenerated and reduced catalyst particles via line 102 can exit the reduction zone 139 and enter into the conversion zone 103. Un-reacted reduction gas can leave the reduction zone as stream 141. If the combustion gas stream 133 includes any entrained catalyst particles, such catalyst particles can be removed via a filter, an electrostatic precipitator, a wet gas scrubber, etc. The separation devices and/or the operating conditions of the separation devices 106 and 132 on the conversion and combustion zones 103 and 104, respectively, can be tuned to deliver a higher or lower amount of entrained catalyst particles in either the second stream 109 or the combustion gas stream 133, depending on the entrained catalyst collection difficulty levels from the second stream 109 vs. the combustion gas stream in line 133.

The second stream 109 can enter into a plenum 110. In the plenum 110, stream 109 can be mixed with a first quench medium stream 111 to produce a cooled second stream in line 112. In some embodiments, the temperature of second stream in line 109 can be >620° C.

In some embodiments, benzene can be produced during the dehydrogenation of the hydrocarbon-containing feed and can be present in the cooled second stream. In some embodiments, benzene can be used as the first quench in line 111. In some embodiments, the first quench medium stream can be in the liquid phase when contacted with the second stream in the plenum 110. In some embodiments, contacting the second steam 109 with the first quench medium stream in line 111 in the plenum 110 can produce a cooled second stream that has a temperature of ≤620° C., ≤610° C., ≤600° C., ≤590° C., or ≤580° C. In some embodiments, the cooled second stream can be at a temperature in a range of ≥550° C. and ≤620° C. or ≤600° C. Reducing the temperature of the second stream in line 109 to less than 600° C. can reduce or stop undesirable thermal reactions of the gas components.

The cooled second stream via line 112 can be introduced into a gas-liquid contacting zone 114 disposed within the quench tower 113. Before entering zone 114, the cooled second stream via line 112 can also pass through one or more heat exchangers for heat recovery. In the gas-liquid contacting zone 114 the cooled second stream can contact a catalyst particle-lean second quench medium stream introduced via line 115 into the quench tower 113. The second quench medium stream in line 115 can be sprayed downward into the gas-liquid contact zone 114 counter-current to the cooled second stream in line 112 to ensure good contact between the cooled second stream and the second quench medium stream. In the gas-liquid contact zone 114 a majority of the catalyst fines and heat in the cooled second stream 112 can be transferred to the second quench medium stream 115 to produce a slurry that can include at least a portion of the second quench in the liquid phase and at least a portion of the entrained coked catalyst particles.

In some embodiments, the second quench medium in stream 115 can have a normal boiling point greater than the first quench medium 111. For example, the normal boiling point of the second quench medium stream 115 can be 150° C. to 580° C.

The slurry can be recovered via line 116 from the quench tower 113. In some embodiments, the slurry can accumulate at the bottom of the quench tower 113 to form a liquid reservoir 117. In some embodiments, a make-up stream via line 129 can be mixed, blended, combined, or otherwise contacted with the slurry in line 116 to produce a combined stream in line 118. The slurry stream in line 116 or the combined stream in line 118 can be cooled in one or more heat exchangers 119 to produce a cooled slurry stream via line 120. At least part of the cooled slurry stream via line 120 can be introduced into a solid-liquid separation device 121 so that the fines-lean second quench medium stream via line 115 can be recovered and a fines-rich second quench medium stream via line 122 can be recovered. One example of the solid-liquid separation device 121 is a filter.

In some embodiments, at least a portion of the fines-rich second quench medium stream in line 122 can be introduced via line 123 into the combustion zone 104. The residual hydrocarbon in the fines-rich second quench medium stream in line 123 can combust to generate heat in the combustion zone 104. The catalyst particles contained in the fines-rich second quench medium stream in line 123 can be regenerated in the combustion zone 104.

In some embodiments, at least a portion of the fines-rich second quench medium stream in line 122 can be sent to a metal reclamation facility 124 where the Group 8-10 element(s) can be reclaimed.

In some embodiments, at the locations above the gas-liquid contact zone 114 in the quench tower 113, the first quench medium, with a normal boiling point less than the second quench medium, can be withdrawn via line 132 from the quench tower, cooled via one or more heat exchangers 126, and a first portion or quantity can be circulated back into the quench tower 113. In some embodiments, a second portion or quantity of the cooled first quench medium can be withdrawn to form a product stream 125, since the first quench medium can be one of the products of alkane dehydrogenation, benzene. In some embodiments, a third portion or quantity of the cooled first quench medium can be recycled to the plenum 110 via line 111 as the first quench medium stream.

At the locations above zone 114 in the quench tower 113, at least a portion of any water present in the quench tower 113 can be withdrawn from the quench tower via line 133, cooled down through one or more heat exchangers 127, and at least a portion of the cooled water can be circulated back into the quench tower 113. A portion or quantity of the cooled water can be withdrawn to via line 128 that can be sent for wastewater treatment.

The overhead product stream 130 coming out of the quench tower 113 can be essentially free of coked catalyst particles and it can then be further cooled, compressed and sent for further product recovery. In some embodiments, the overhead product stream in line 130 can be passed through one or more gas-solid separators to remove at least a portion of any entrained catalyst particles if present.

Figure 2:
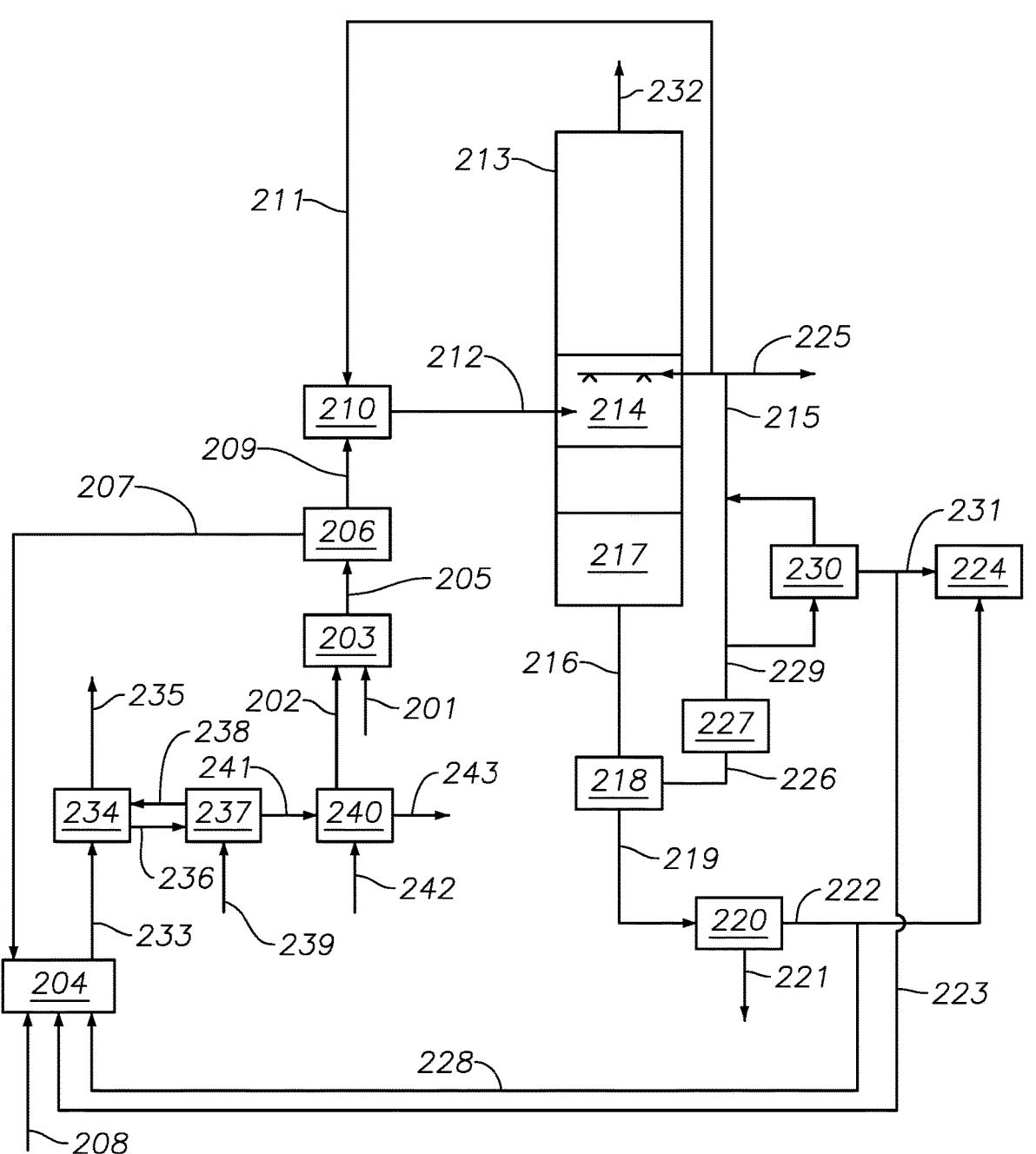
FIG. 2 depicts another system for dehydrogenating a hydrocarbon-containing feed that includes a reactor or conversion zone, a regenerator or combustion zone, and a quench tower, according to one or more embodiments described.

FIG. 2 depicts another system for dehydrogenating a hydrocarbon-containing feed in line 201 that includes a reactor or conversion zone 203, a regenerator or combustion zone 204, an oxygen soaking zone 237, a reduction zone 240, and a quench tower 213, according to one or more embodiments. The hydrocarbon containing feed via line 201 can be introduced into the conversion zone 203, e.g., at a bottom end of a riser reactor or an upper end of a downer reactor. In some embodiments, the hydrocarbon-containing feed in line 201 can include steam. Regenerated and reduced catalyst particles via line 202 can be conveyed from the reduction zone 240 to the conversion zone 203. The hydrocarbon-containing feed can be contacted with the regenerated and reduced catalyst particles in the conversion zone 203 to effect dehydrogenation of at least a portion of the hydrocarbon-containing feed to produce a conversion effluent via line 205 that can include coked catalyst particles, one or more dehydrogenated hydrocarbons, unreacted hydrocarbon-containing feed, steam, benzene, or any mixture thereof.

The conversion effluent via line 205 can be introduced into one or more separation devices 206, e.g., one or more cyclones, that can separate the conversion effluent into a first stream 207 rich in the coked catalyst particles and lean in the one or more dehydrogenated hydrocarbons and a second stream via line 209 rich in the one or more dehydrogenated hydrocarbons that includes entrained coked catalyst particles.

The first stream via line 207 can be recycled to the combustion zone 204. In some embodiments, the first stream in line 207 can include entrained gaseous components such as the one or more dehydrogenated hydrocarbons, unreacted hydrocarbon-containing feed, steam, or a mixture thereof. In such embodiment, at least a portion of the gaseous components in the first stream in line 207 can be stripped off before the first stream is introduced into the combustion zone 204. An oxidant and optionally a fuel via line 208 can be introduced into the combustion zone 204 that can contact at least a portion of the coked catalyst particles in the first stream to effect combustion of at least a portion of the coke, and, if present, the fuel to produce a combustion effluent that includes the regenerated catalyst particles and a combustion gas. The combustion of the coke and, if present fuel, can produce heat to burn the coke from the coked catalyst particles, re-disperse the Group 8-10 element(s) on the spent catalyst particles and add heat to the regenerated catalyst particles.

The combustion effluent can be recovered via line 233 and can enter into one or more separation devices 234, e.g., one or more cyclones, to be separated into a stream 236 that contains a majority of any catalyst particles entrained in the combustion effluent and a small amount of entrained combustion gas and a combustion gas stream 235 that contains a majority of the combustion gas and, if any, a small amount of entrained catalyst particles. In some embodiments, the one or more separation devices 234 can include three or more stages of cyclones to achieve a higher solid recovery efficiency from the combustion effluent in line 233 and to reduce the amount of entrained catalyst particles in the combustion gas stream 235.

Stream 236 can be sent to an oxygen soaking zone 237. A relatively dry oxidant gas stream 239 can be fed into the oxygen soaking zone 237 to fully regenerate the catalyst. After entering into zone 237, any un-reacted dry oxidant gas stream may entrain fully regenerated catalyst particles and exit zone 237 as stream 238. Stream 238 can enter into the separation device 234 and be split into a solid stream and a gas stream. The solid stream rich in fully regenerated catalyst particles can join stream 236 and return to zone 237. The gas stream rich in the unreacted dry oxidant gas can join stream 235. The fully regenerated catalyst particles can leave zone 237 as stream 241 and enter into the reduction zone 240. A reduction gas stream 242 can also be fed into zone 240. The regenerated and reduced catalyst particles via line 202 can exit the reduction zone 240 and enter into the conversion zone 203. Any un-reacted reduction gas can leave the reduction zone as stream 243.

In some embodiments, if the combustion gas stream 235 includes any entrained catalyst particles, it can be passed through a filter, an electrostatic precipitator, a wet gas scrubber, etc. The separation devices 206 and 234 on the conversion and combustion zones 203 and 204, respectively, can be tuned to deliver a higher or lower amount of entrained catalyst particles in either the second stream 209 or the combustion gas stream 233 depending on the entrained catalyst collection difficulty levels from the second stream in line 209 vs. the combustion gas stream in line 235.

The second stream 209 can enter into a plenum 210. In the plenum 210, stream 209 can be mixed with a first quench medium stream 211 to produce a cooled second stream in line 212. In some embodiments, the temperature of second stream in line 209 can be >620° C.

In some embodiments, benzene can be produced during the dehydrogenation of the hydrocarbon-containing feed and can be present in the cooled second stream. In some embodiments, benzene can be used as the first quench medium in line 211. In some embodiments, the first quench medium stream can be in the liquid phase when contacted with the second stream in the plenum 210. In some embodiments, contacting the second steam 209 with the first quench medium stream in line 211 in the plenum 210 can produce a cooled second stream that has a temperature of ≤620° C., ≤610° C., ≤600° C., ≤590° C., or ≤580° C. In some embodiments, the cooled second stream can be at a temperature in a range of ≥550° C. and ≤620° C. or ≤600° C. Reducing the temperature of the second stream in line 209 to less than 600° C. can reduce or stop undesirable thermal reactions of the gas components.

The cooled second stream via line 212 can be introduced into a gas-liquid contacting zone 214 disposed within the quench tower 213. Before entering zone 214, the cooled second stream via line 212 may also travel through one or more heat exchangers for heat recovery. In the gas-liquid contacting zone 214 the cooled second stream can contact a catalyst particle-lean second quench medium stream introduced via line 215 into the quench tower 213. The second quench medium stream in line 215 can be sprayed downward into the gas-liquid contact zone 214 counter-current to the cooled second stream in line 212 to ensure good contact between the cooled second stream and the second quench medium stream. In the gas-liquid contact zone 214 a majority of the catalyst fines and heat in the cooled second stream 212 can be transferred to the second quench medium stream 215 to produce a slurry that can include the first quench medium and the second quench medium in the liquid phase and at least a portion of the coked catalyst particles.

The slurry can be recovered via line 216 from the quench tower 213. In some embodiments, the slurry can accumulate at the bottom of the quench tower 213 to form a liquid reservoir 217. The liquid reservoir can also include unreacted water that can be added as a reactant in the hydrocarbon-containing feed. The slurry stream in line 216 can be introduced into a separation device 218 to produce a water stream that includes coked catalyst particles via line 219 and a quench medium stream that includes coked catalyst particles via line 226.

The water stream via line 219 can be introduced into a separation device 220 to produce a coked catalyst particles containing water stream via line 222 and a water stream lean in the coked catalyst particles via line 221. In some embodiments, the separation device 220 can be a liquid-solid filter. The wastewater stream via line 221 can be sent to a wastewater treatment facility. In some embodiments, at least a portion of the coked catalyst particles containing water stream via line 222 can be conveyed to a metal reclamation facility 224, conveyed via line 228 to the combustion zone 204, or a combination thereof.

The quench medium stream via line 226 can be introduced into one or more heat exchangers 227 to produce a cooled quench medium stream via line 229. The cooled quench medium stream via line 229 can be introduced into one or more solid-liquid separation devices 230 to produce a quench medium stream lean in the coked catalyst particles via line 215 and a quench medium stream rich in the coked catalyst particles via line 231. In some embodiments, the solid-liquid separation device 230 can be a liquid-solid filter.

In some embodiments, at least a portion of the quench medium stream rich in the coked catalyst particles can be conveyed via line 231 to the metal reclamation facility 224, conveyed via line 223 to the combustion zone 204, or a combination thereof. If at least a portion of the quench medium stream rich in the coked catalyst particles via line 223 is conveyed to the combustion zone 204 the residual hydrocarbon therein can combust within the conversion zone 204 to produce heat and the coked catalyst particles can be regenerated therein. In some embodiments, a first portion of the quench medium stream lean in the coked catalyst particles via line 215 can recycled into the quench tower 213 as the second quench medium, a second portion of the quench medium stream lean in the coked catalyst particles via line 215 can recycled via line 211 into the plenum 210 as the first quench medium, and, optionally, a third portion of the quench medium stream lean in the coked catalyst particles in line 215 can be recovered via line 225 as a product.

The overhead product stream 232 coming out of the quench tower 213 can be essentially free of coked catalyst particles and it can then be further cooled, compressed and sent for further product recovery. In some embodiments, the overhead product stream in line 232 can be passed through one or more gas-solid separators to remove at least a portion of any entrained catalyst particles if present.

EXAMPLES

The foregoing discussion can be further described with reference to the following non-limiting examples.

Catalyst Composition 1: was prepared by mixing CATAPAL® D pseudoboehmite (Sasol) (47 g) and calcined Mg—Al hydrotalcite (PURALOX® MG70) (44 g) that contained 70 wt % MgO and 30 wt % $Al_2O_3$ in deionized water (524 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % $Al_2O_3$ derived from CATAPAL® D. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 50:50 MG70: CATAPAL® D.

Catalyst Composition 2: was prepared by mixing 40 wt % aluminum chlorohydrol solution (ACH) (85 g) and calcined Mg—Al hydrotalcite (PURALOX® MG70) (88 g) in deionized water (596 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 80 wt % PURALOX® MG70 and 20 wt % $Al_2O_3$ derived from ACH. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 80:20 MG70:ACH.

Catalyst Compositions 3-16 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 m²/g, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours. Table 1 shows the nominal Pt and Sn content of each catalyst composition based on the weight of the support.

TABLE 1

| Catalyst | Pt (wt %) | Sn (wt %) |
|---|---|---|
| 3 | 0.4 | 1 |
| 4 | 0.3 | 1 |
| 5 | 0.2 | 1 |
| 6 | 0.1 | 1 |
| 7 | 0.05 | 1 |
| 8 | 0.025 | 1 |
| 9 | 0.0125 | 1 |
| 10 | 0 | 1 |
| 11 | 0.1 | 0.5 |
| 12 | 0.1 | 1 |
| 13 | 0.1 | 2 |
| 14 | 0.0125 | 0 |
| 15 | 0.0125 | 0.5 |
| 16 | 0.0125 | 2 |

Examples Using the Catalyst Compositions 1 and 2 Described Above.

Fixed bed experiments were conducted at ~100 kPa-absolute. A gas chromatograph (GC) was used to measure the composition of the reactor effluents. The concentration of each component in the reactor effluents were then used to calculate the $C_3H_6$ yield and selectivity. The $C_3H_6$ yield and selectivity, as reported in these examples, were calculated on the carbon mole basis.

In each example, 0.3 g of catalyst Mcat was mixed with an appropriate amount of quartz diluent and loaded into a quartz reactor. The amount of diluent was determined so that the catalyst bed (catalyst+diluent) overlapped with the iso-thermal zone of the quartz reactor and the catalyst bed was largely isothermal during operation. The dead volume of the reactor was filled with quartz chips/rods.

The concentration of each component in the reactor effluent was used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the table below.

The process steps for Examples 1 and 2 were as follows:
1. The system was flushed with an inert gas.
2. An oxygen containing gas (Ogas) at a flow rate ($F_{regen}$) was flown through the by-pass of the reaction zone, while an inert was flown through the reaction zone. The reaction zone was heated to a regeneration temperature $T_{regen}$.
3. The oxygen containing gas was then flown through the reaction zone for a certain period of time ($t_{regen}$) to regenerate the catalyst. After $t_{regen}$, the temperature within the reaction zone was changed from $T_{regen}$ to a reduction temperature ($T_{red}$) while maintaining the oxygen-containing gas flow.
4. The system was flushed with an inert gas.
5. A $H_2$ containing gas (Hgas) at a flow rate ($F_{red}$) was flown through the by-pass of the reaction zone for a certain period of time, while an inert was flown through the reaction zone. This is then followed by flowing the $H_2$ containing gas through the reaction zone at $T_{re}$a for a certain period of time ($t_{red}$).
6. The system was flushed with an inert. During this process, the temperature of the reaction zone was changed from $T_{red}$ to a reaction temperature of 655° C.
7. A hydrocarbon-containing (HCgas) feed that included 81 vol % $C_3H_8$, 9 vol % inert (Ar or Kr) and 10 vol % steam at a flow rate ($F_{rxn}$) was flown through the by-pass of the reaction zone for a certain period of time, while an inert was flown through the reaction zone. The hydrocarbon-containing feed was then flown through the reaction zone at 655° C. for 10 min. GC sampling of the reaction effluent started as soon as the feed was switched from the by-pass of the reaction zone to the reaction zone.

Figure 3:
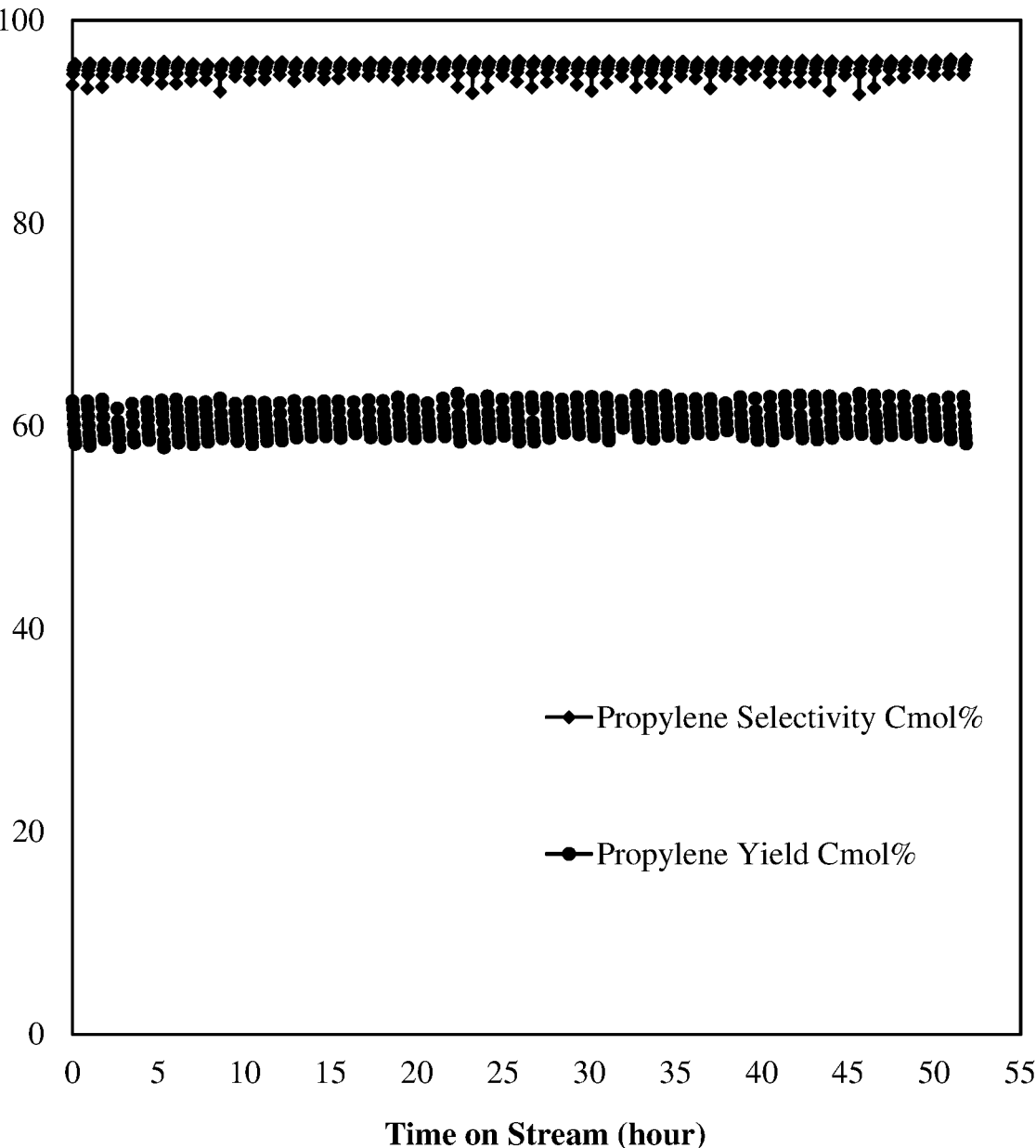
FIG. 3 shows a catalyst composition was stable for over 60 cycles for propane dehydrogenation.

The above process steps were repeated in cycles until stable performance was obtained. Table 2 shows that both Catalyst 1 and Catalyst 2 were active/selective for propane dehydrogenation. FIG. 3, a graph showing propylene selectivity in Cmol % and propylene yield in Cmol % as a function of time on stream, demonstrates that catalyst 2 was stable over 60 cycles for propane dehydrogenation.

TABLE 2

| Catalyst | 1 | 2 |
|---|---|---|
| $M_{cat}$ (g) | 0.3 | 0 |
| $F_{rxn}$ (sccm) | 17.6 | 17.6 |
| Hgas | 10% $H_2$; 90% Ar | 10% $H_2$; 90% Ar |
| $F_{red}$ (sccm) | 46.6 | 46.6 |
| $T_{red}$ (° C.) | 800 | 800 |
| $t_{red}$ (min) | 0.05 | 0.05 |
| Ogas | 90% Air, 10% $H_2O$; Then Dry air | 90% Air, 10% $H_2O$; Then Dry air |
| $F_{regen}$ (sccm) | 93.2 Then 83.9 | 93.2 Then 83.9 |
| $T_{regen}$ (° C.) | 800 | 800 |
| $t_{regen}$ (min) | 1; Then 10 | 1; Then 10 |

TABLE 2-continued

| Performance | $Y_{ini}$ | 59.4 | 62.9 |
|---|---|---|---|
| | $Y_{end}$ | 52.4 | 59.2 |
| | $S_{ini}$ | 95.3 | 94.4 |
| | $S_{end}$ | 96.3 | 95.9 |

Examples using the Catalyst Compositions 3 to 16 described above.

Fixed bed experiments were conducted at approximately 100 kPa-absolute that used catalyst compositions 3-16. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in Tables 3 and 4 below for catalyst compositions 3-10.

The process steps for catalyst compositions 3-10 were as follows:

1. The system was flushed with an inert gas.
2. Dry air at a flow rate of 83.9 sccm was passed through a by-pass of the reaction zone, while an inert was passed through the reaction zone. The reaction zone was heated to a regeneration temperature of 800° C.
3. Dry air at a flow rate of 83.9 sccm was then passed through the reaction zone for 10 min to regenerate the catalyst.
4. The system was flushed with an inert gas.
5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds.
6. The system was flushed with an inert gas. During this process, the temperature of the reaction zone was changed from 800° C. to a reaction temperature of 670° C.
7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone.

The above process steps were repeated in cycles until stable performance was obtained. Tables 3 and 4 show that catalyst composition 8 that contained only 0.025 wt % of Pt and 1 wt % of Sn had both a similar yield and a similar selectivity as compared to catalyst composition 3 that contained 0.4 wt % of Pt and 1 wt % of Sn, which was surprising and unexpected. Catalyst composition 10 that did not include any Pt did not show an appreciable propylene yield.

TABLE 3

| | | Catalyst 3 | Catalyst 4 | Catalyst 5 | Catalyst 6 |
|---|---|---|---|---|---|
| Performance | $Y_{ini}$ | 61.7 | 61.7 | 60.7 | 63.7 |
| | $Y_{end}$ | 55.2 | 55.7 | 54.2 | 56.7 |
| | $S_{ini}$ | 97.3 | 97.2 | 97.0 | 97.1 |
| | $S_{end}$ | 98.1 | 98.0 | 97.7 | 98.3 |

TABLE 4

| | | Catalyst 7 | Catalyst 8 | Catalyst 9 | Catalyst 10 |
|---|---|---|---|---|---|
| Performance | $Y_{ini}$ | 62.4 | 62.0 | 56.7 | 2.0 |
| | $Y_{end}$ | 57.2 | 54.6 | 45.7 | 1.7 |
| | $S_{ini}$ | 96.7 | 97.3 | 96.9 | 64.2 |
| | $S_{end}$ | 97.7 | 98.0 | 97.6 | 49.5 |

Catalyst compositions 11-16 were also tested using the same process steps 1-7 described above with regard to catalysts 3-10. Table 5 shows that the level of Sn should not be too low or too high for optimal propylene yield for the catalyst compositions that included 0.1 wt % of Pt based on the weight of the support.

TABLE 5

| | | Catalyst 11 0.5 wt % Sn | Catalyst 6 1 wt % Sn | Catalyst 12 1 wt % Sn | Catalyst 13 2 wt % Sn |
|---|---|---|---|---|---|
| Performance | $Y_{ini}$ | 58.4 | 63.7 | 63.4 | 56.5 |
| | $Y_{end}$ | 49.5 | 56.7 | 55.5 | 47.7 |
| | $S_{ini}$ | 96.9 | 97.1 | 97.2 | 97.8 |
| | $S_{end}$ | 97.6 | 98.3 | 98.1 | 98.2 |

Table 6 shows that the level of Sn should not be too high or too low for optimal propylene yield for the catalyst compositions that included 0.0125 wt % of Pt based on the weight of the support.

TABLE 6

| | | Catalyst 14 0 wt % Sn | Catalyst 15 0.5 wt % Sn | Catalyst 9 1 wt % Sn | Catalyst 16 2 wt % Sn |
|---|---|---|---|---|---|
| Performance | $Y_{ini}$ | 2.6 | 44 | 56.7 | 55.4 |
| | $Y_{end}$ | 1.7 | 24.4 | 45.7 | 44.1 |
| | $S_{ini}$ | 63.9 | 96.7 | 96.9 | 96.8 |
| | $S_{end}$ | 61.1 | 95.6 | 97.6 | 97.6 |

Figure 4:
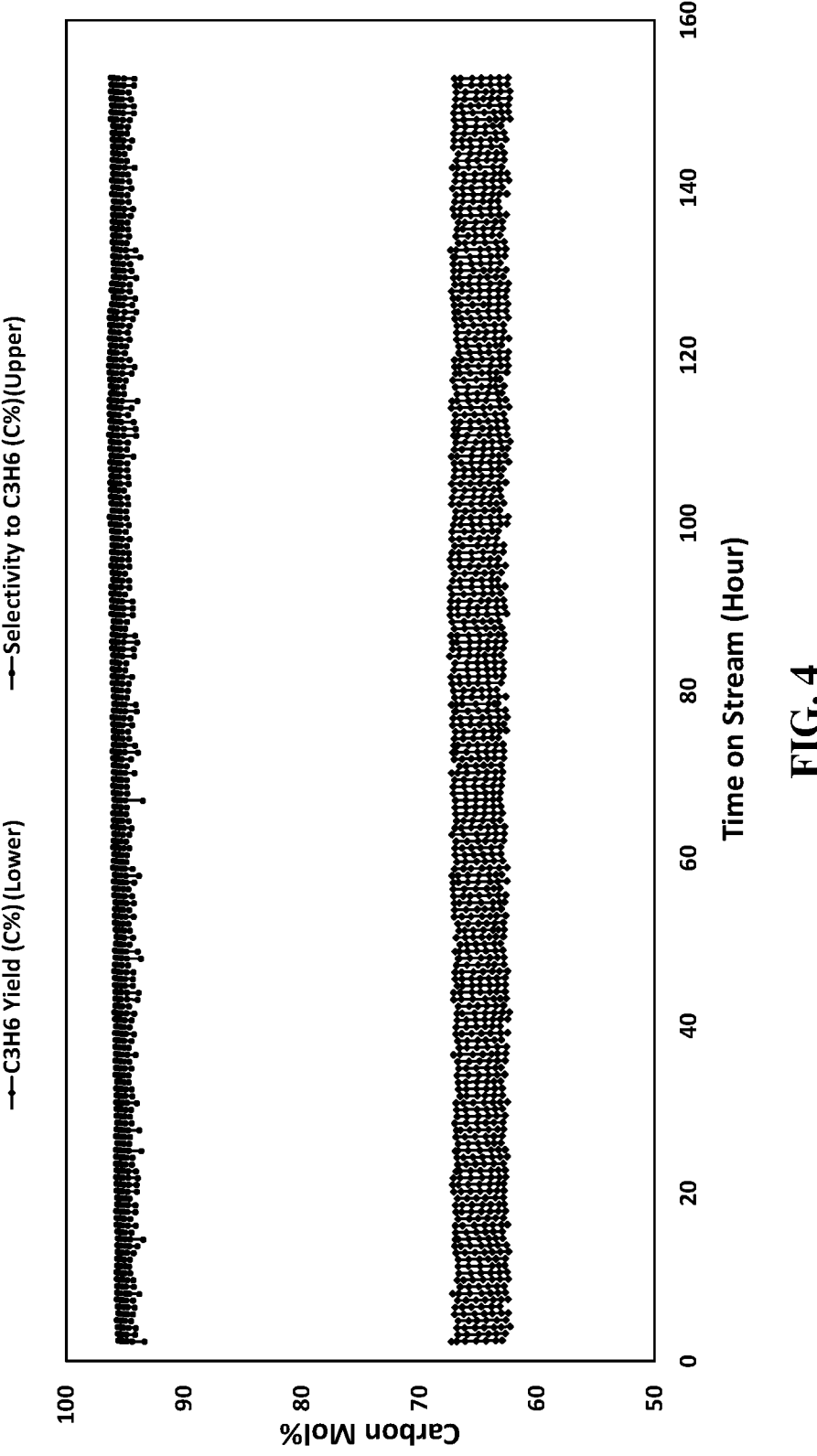
FIG. 4 shows a catalyst composition (catalyst 8) maintained its performance for 204 cycles.

Catalyst composition 8 that contained only 0.025 wt % of Pt and 1 wt % of Sn was also subjected to a longevity test using the same process steps 1-7 described above with regard to catalyst compositions 3 to 10, except a flow rate of 17.6 sccm was used instead of 35.2 sccm in step 7. FIG. 4 shows that catalyst composition 8 maintained performance for 204 cycles (x-axis is time, y-axis is $C_3H_6$ yield and selectivity to $C_3H_6$, both in carbon mole %).

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:
(I) contacting a hydrocarbon-containing feed with fluidized dehydrogenation catalyst particles in a conversion zone to effect dehydrogenation of at least a portion of the hydrocarbon-containing feed to produce a conversion effluent comprising coked catalyst particles and one or more dehydrogenated hydrocarbons;
(II) separating from the conversion effluent a first stream rich in the coked catalyst particles and lean in the one or more dehydrogenated hydrocarbons and a second stream rich in the one or more dehydrogenated hydrocarbons and comprising entrained coked catalyst particles;
(III) contacting the second stream with a first quench medium to produce a cooled second stream;
(IV) contacting the cooled second stream with a second quench medium within a quench tower;
(V) recovering a gaseous stream comprising the one or more dehydrogenated hydrocarbons, a condensed first quench medium stream, and a slurry stream comprising at least a portion of the second quench medium in a liquid phase and the entrained coked catalyst particles from the quench tower;
(VI) recycling at least a portion of the condensed first quench medium to step (III);
(VII) separating at least a portion of the entrained coked catalyst particles from the slurry stream to provide a recovered second quench medium stream and a recovered entrained coked catalyst particles stream; and
(VIII) recycling at least a portion of the recovered second quench medium stream to step (IV).

2. The process of claim 1, further comprising:
(IX) contacting at least a portion of the coked catalyst particles in the first stream and at least a portion of the coked catalyst particles in the recovered entrained catalyst particles stream with an oxidant and optionally a fuel in a combustion zone to effect combustion of at least a portion of the coke and, if present, the fuel to produce a combustion effluent comprising regenerated catalyst particles lean in coke and a combustion gas;
(X) separating a combustion gas stream and a regenerated catalyst particles stream; and
(XI) contacting an additional quantity of the hydrocarbon-containing feed with fluidized regenerated catalyst particles from the regenerated catalyst particles stream to produce additional conversion effluent comprising recoked catalyst particles and additional one or more dehydrogenated hydrocarbons.

3. The process of claim 1, wherein the dehydrogenation catalyst particles comprise a Group 8-10 element disposed on a support, the process further comprising:
(XII) conveying at least a portion of the recovered entrained catalyst particles stream to a metal reclamation facility; and
(XIII) recovering at least a portion of the Group 8-10 element from the coked catalyst particles in the recovered entrained coked catalyst particles stream.

4. The process of claim 1, further comprising (XIV) cooling the slurry stream prior to step (VII) to produce a cooled slurry stream.

5. The process of claim 1, wherein the conversion effluent further comprises benzene, the process further comprising (XV) withdrawing a benzene product stream from the quench tower.

6. The process of claim 5, wherein the first quench medium comprises at least a portion of the benzene product stream withdrawn from the quench tower.

7. The process of claim 1, wherein the first stream and the second stream are separated from the conversion effluent within one or more cyclones, and wherein the second stream is contacted with the first quench medium within at least one plenum of the one or more cyclones.

8. The process of claim 1, wherein the first stream and the second stream are separated from the conversion effluent in a primary separation device and a secondary separation device downstream of and in fluid communication with the primary separation device, and wherein the second stream is contacted with the first quench medium within a plenum of the secondary separation device.

9. The process of claim 1, wherein the first stream and the second stream are separated from the conversion effluent within one or more gas/solid separators, and wherein the second stream is contacted with the first quench medium within a transfer line in fluid communication with the one or more gas/solid separators and the quench tower.

10. The process of claim 1, wherein the first quench medium is in a liquid phase when contacted with the second stream, and wherein the first quench medium is in a gas phase after contacting the second stream.

11. The process of claim 1, wherein the first quench medium comprises benzene, water, or a polyaromatic hydrocarbon having a normal boiling point of <580° C., or a mixture thereof.

12. The process of claim 1, wherein the second quench medium comprises benzene, water, or a polyaromatic hydrocarbon having a normal boiling point of <580° C., or a mixture thereof.

13. The process of claim 1, wherein the second quench medium has a normal boiling point that is greater than a normal boiling point of the first quench medium.

14. The process of claim 1, wherein a bottom zone within the quench tower contains an inventory of the slurry stream.

15. The process of claim 1, wherein the entrained coked catalyst particles are separated from the slurry stream in step (VII) via one or more filters.

16. The process of claim 1, wherein the first quench medium comprises a liquid hydrocarbon, and wherein any non-solid components in the cooled second stream are completely in the vapor phase.

17. The process of claim 1, wherein the first quench medium comprises an aromatic hydrocarbon that is formed during dehydrogenation of the hydrocarbon-containing feed.

18. The process of claim 1, wherein the second quench medium comprises an aromatic hydrocarbon that is not formed during dehydrogenation of the hydrocarbon-containing feed.

19. The process of claim 1, wherein the second quench medium counter-currently contacts the cooled second stream within the quench tower.

20. The process of claim 1, wherein the conversion effluent is at a temperature of ≥620° C. and the cooled second stream is at a temperature of ≥500° C. and <620° C.

21. The process of claim 1, wherein the dehydrogenation catalyst particles comprise 0.001 wt % to 6 wt % of a Group 8-10 element and optionally up to 10 wt % of a promoter comprising Sn, Cu, Au, Ag, Ga, a combination thereof, or a mixture thereof disposed on a support, and wherein all weight percent values are based on the weight of the support.

22. The process of claim 1, wherein the dehydrogenation catalyst particles comprise 0.001 wt % to 6 wt % of Pt and optionally up to 10 wt % of a promoter comprising Sn, Cu, Au, Ag, Ga, a combination thereof, or a mixture thereof disposed on a support, wherein the support comprises at least 0.5 wt % of a Group 2 element, and wherein all weight percent values are based on the weight of the support.

23. The process of claim 1, wherein the dehydrogenation catalyst particles have a median particle size in a range from 10 μm to 500 μm and an apparent loose bulk density in a range from 0.3 g/cm$^3$ to 2 g/cm$^3$, as measured according to ASTM D7481-18 modified with a 10, 25, or 50 mL graduated cylinder instead of a 100 or 250 mL graduated cylinder.

24. The process of claim 1, wherein dehydrogenation catalyst particles meet the requirements of a Geldart A or Geldart B classification.

\* \* \* \* \*